US009499595B2

(12) United States Patent
Krug et al.

(10) Patent No.: US 9,499,595 B2
(45) Date of Patent: Nov. 22, 2016

(54) DEVELOPMENT OF INFLUENZA A ANTIVIRALS

(75) Inventors: Robert M. Krug, Austin, TX (US); Karen Y. Twu, San Mateo, CA (US)

(73) Assignee: BOARD OF REGENTS, THE UNIVERSITY OF TEXAS SYSTEMS, Austin, TX (US)

( * ) Notice: Subject to any disclaimer, the term of this patent is extended or adjusted under 35 U.S.C. 154(b) by 143 days.

(21) Appl. No.: 12/554,767

(22) Filed: Sep. 4, 2009

(65) Prior Publication Data

US 2010/0107264 A1    Apr. 29, 2010

Related U.S. Application Data

(62) Division of application No. 11/566,214, filed on Dec. 2, 2006, now Pat. No. 7,601,490.

(60) Provisional application No. 60/741,764, filed on Dec. 2, 2005, provisional application No. 60/852,361, filed on Oct. 16, 2006.

(51) Int. Cl.

| C07K 14/47 | (2006.01) |
|---|---|
| C07K 14/705 | (2006.01) |
| C07K 14/005 | (2006.01) |
| C12N 7/04 | (2006.01) |
| C12N 7/00 | (2006.01) |
| C12N 5/16 | (2006.01) |
| A61K 39/00 | (2006.01) |
| A61K 38/17 | (2006.01) |
| A61K 38/16 | (2006.01) |
| C12N 5/0783 | (2010.01) |

(52) U.S. Cl.
CPC ............... *C07K 14/47* (2013.01); *A61K 38/16* (2013.01); *A61K 38/17* (2013.01); *A61K 39/0008* (2013.01); *A61K 2039/55516* (2013.01); *C07K 14/005* (2013.01); *C07K 14/705* (2013.01); *C12N 5/0636* (2013.01); *C12N 5/163* (2013.01); *C12N 7/00* (2013.01); *C12N 7/04* (2013.01); *C12N 2760/16111* (2013.01); *C12N 2760/16134* (2013.01); *Y10S 514/888* (2013.01)

(58) Field of Classification Search
CPC ............... A61K 2039/55516; A61K 38/16; A61K 38/17; A61K 39/0008; A61K 39/145; A61K 39/12; A61K 38/00; A61K 48/005; C12N 5/0636; C12N 5/163; C12N 7/04; C12N 7/00; C12N 2760/16134; C12N 2760/16122; C12N 2760/16162; C12N 2760/16234; C12N 2760/16143; C12N 2760/16151; C12N 2760/16222; C12N 2760/16121; C12N 2760/16161; C12N 2760/16171; C12N 2760/16061; C12N 2760/16111; C12N 15/1131; C07K 14/005; C07K 14/47; C07K 14/705; C07K 14/7051; C07K 2319/33; C07K 14/435; C07K 14/11; C07K 14/4702; C07K 16/1018
See application file for complete search history.

(56) References Cited

U.S. PATENT DOCUMENTS

| 6,593,091 B2 | 7/2003 | Keys et al. |
| 7,601,490 B2 * | 10/2009 | Krug et al. ................. 435/5 |
| 7,709,190 B2 * | 5/2010 | Montelione et al. ............ 435/5 |
| 8,455,621 B2 * | 6/2013 | Krug et al. .................. 530/350 |
| 8,796,008 B2 * | 8/2014 | Montelione et al. ......... 435/236 |
| 2005/0053985 A1 * | 3/2005 | Trotta et al. ...................... 435/6 |
| 2005/0191703 A1 | 9/2005 | Palese et al. |
| 2005/0233963 A1 | 10/2005 | Moseley et al. |
| 2010/0247569 A1 | 9/2010 | Montelione et al. |

FOREIGN PATENT DOCUMENTS

| WO | 2004043404 A2 | 5/2004 |
| WO | 2007061969 A2 | 5/2007 |
| WO | 2008048306 A2 | 4/2008 |

OTHER PUBLICATIONS

Nemeroff, et al. Influenza Virus NS1 Protein Interacts with the Cellular 30 kDa Subunit of CPSF and Inhibits 39 End Formation of Cellular Pre-mRNAs. Molecular Cell, vol. 1, 991-1000, Jun. 1998.*
Noah, et al. Cellular antiviral responses against influenza A virus are countered at the posttranscriptional level by the viral NS1A protein via its binding to a cellular protein required for the 3' end processing of cellular pre-mRNAS. Virology, vol. 307, Issue 2, Mar. 15, 2003, pp. 386-395.*
Strausberg RL, et. al. Cpsf4 protein [Mus musculus]. GenBank: AAH57067.1. Dep. Oct. 8, 2003.*
Barabino, S. M., et al., "The 30-kD subunit of mammalian cleavage and polyadenylation specificity factor and its yeast homolog are RNA-binding zinc finger proteins." Genes Dev (1997), 11:1703-16.
CDC (Center for Disease Control). 2005. Key facts about influenza and the influenza vaccine. http://www.cdc.gov/flu/keyfacts.htm.
Chen, Z., Y. Li, et al., "Influenza A virus NS1 protein targets poly(A)-binding protein II of the cellular 3'-end processing machinery." EMBO J (1999), 18:2273-83.
Cox, N. J., et al., "Influenza." Lancet (1999), 354:1277-82.
Ferguson, N. M., et al., "Strategies for containing an emerging influenza pandemic in Southeast Asia." Nature (2005), 437:209-14.
Geiss, G. K., et al., "Cellular transcriptional profiling in influenza A virus-infected lung epithelial cells: the role of the nonstructural NS1 protein in the evasion of the host innate defense and its potential contribution to pandemic influenza." Proc Nati Acad Sci U S A (2002), 99:10736-41.
Kim, M. J., et al., "Human influenza viruses activate an interferon-independent transcription of cellular antiviral genes: outcome with influenza A virus is unique." Proc Natl Acad Sci U S A (2002), 99:10096-101.

(Continued)

*Primary Examiner* — Rachel B Gill
(74) *Attorney, Agent, or Firm* — Parker Highlander PLLC

(57) ABSTRACT

The present invention includes compositions, methods and systems to isolate and characterize novel antiviral agents by contacting the antiviral agent with the F2F3 zinc fingers of a CPSF30 protein and an Influenza A NS1A protein; and determining whether the binding between the CPSF30 protein and the Influenza A NS1A protein is reduced.

3 Claims, 9 Drawing Sheets

(56) References Cited

OTHER PUBLICATIONS

Kiso, M., K. et al., "Resistant influenza A viruses in children treated with oseltamivir: descriptive study." Lancet (2004), 364:759-65.
Le, Q. M., et al., "Avian flu: isolation of drug-resistant H5N1 virus." Nature (2005), 437:1108.
Li, Y., et al., "The 3'-end-processing factor CPSF is required for the splicing of single-intron pre-mRNAs in vivo." RNA (2001), 7:920-31.
Longini, I. M., Jr., et al., "Containing pandemic influenza at the source." Science (2005), 309:1083-7.
Longtine, M. S., et al., "Additional modules for versatile and economical PCR-based gene deletion and modification in *Saccharomyces cerevisiae*." Yeast (1998), 14:953-61.
Nemeroff, M. E., et al., "The influenza virus NS1 protein forms multimers in vitro and in vivo." Virology (1995), 212:422-8.
Nemeroff, M. E., et al., "Influenza virus NS1 protein interacts with the cellular 30 kDa subunit of CPSF and inhibits 39 End Formation of Cellular pre-mRNAs." Mol Cell (1998), 1:991-1000.
Noah, D. L., et al., "Cellular antiviral responses against influenza A virus are countered at the posttranscriptional level by the viral NS1A protein via its binding to a cellular protein required for the 3' end processing of cellular pre-mRNAS." Virology (2003), 307:386-95.
Ohnishi, et al., "Mechanism of Host Defense Suppression Induced by Viral Infection: Mode of Action of Inosiplex as an antiviral Agent," Infection and Immunity (1982) vol. 38 vol. 1 243-250.
Puthavathana, P., et al., "Molecular characterization of the complete genome of human influenza H5N1 virus isolates from Thailand." J Gen Virol (2005), 86:423-33.
Qiu, Y., et al., "The influenza virus NS1 protein is a poly(A)-binding protein that inhibits nuclear export of mRNAs containing poly(A)." J Virol (1994), 68:2425-32.
Reid, A. H., et al., "The 1918 Spanish influenza: integrating history and biology." Microbes Infect (2001), 3:81-87.
Shimizu, K., A. Iguchi, R. Gomyou, and Y. Ono. 1999. Influenza virus inhibits cleavage of the HSP70 pre-mRNAs at the polyadenylation site. Virology (1999), 254:213-9.
Suzuki, H., et al., "Emergence of amantadine-resistant influenza A viruses: epidemiological study." J Infect Chemother (2003), 9:195-200.
Yoneyama, et al., "Direct triggering of the type I interferon system by virus infection: activation of a transcription factor complex containing IRF-3 and CBP/p300," The EMBO Journal (1998) vol. 17 No. 4 pp. 1087-1095.
Yuan, W., et al., "Influenza B virus NS1 protein inhibits conjugation of the interferon (IFN)-induced ubiquitin-like ISG15 protein." EMBO J (2001), 20:362-71.
Elton, et al. "Identification of Amino Acid Residues of Influenza Virus Nucleoprotein Essential for RNA Binding" Journal of Virology, Sep. 1999, pp. 7357-7367.
Greenspan, et al. "Two Nuclear Location Signals in the Influenza Virus NS1 Nonstructural Protein" Journal of Virology, Aug. 1988, pp. 3020-3026.
International Search Report and Written Opinion for PCT/US2006/046234 dated Dec. 21, 2007.
International Search Report and Written Opinion for PCT/US2006/046239 dated May 2, 2008.
Twu, et al. "The CPSF30 Binding Site on the NS1A Protein of influenza A virus is a potential antiviral Target" J. Virol. Apr. 2006, vol. 80, No. 8, pp. 3957-3965.
Salvatore, et al. Virus versus host: modulation of the host α/β interferon pathways by the influenza A virus NS1 protein, International Congress Series 1219 (2001) 513-520.
Rice, et al. "Inhibitors of HIV Nucleocapsid Protein Zinc Fingers as Candidates for the Treatment of AIDS" Science, Nov. 17, 1995; 270, 5239, Research Library, p. 1194.
WHO (World Health Organization). 2005. Avian influenza. http://www.who.int/csr/disease/avian_influenza/en/; Avian Influenza A (H5N1) Infection in Humans, The Writing Committee of the World Health Organization (WHO) Consultation on Human Influenza A/H5. (New England Journal of Medicine, 2005, 353:1374-1385.).

\* cited by examiner

A

Myc Ab

B

Inhibition of the 3' end processing of cellular pre-mRNAs, including IFN-β pre-mRNA, enabling influenza A virus to replicate efficiently The 3' end processing of cellular pre-mRNAs, including IFN-β pre-mRNA, is NOT inhibited, resulting in inhibition of the replication of influenza A virus

Figure 8

SEQUENCE LISTING

```
<160> NUMBER OF SEQ ID NOS: 15

<210> SEQ ID NO 1
<211> LENGTH: 813
<212> TYPE: DNA
<213> ORGANISM: Homo sapiens

<400> SEQUENCE: 1
atgcaggaaa tcatcgccag cgtggaccac atcaagtttg acttggagat cgcggtggag     60
cagcagctgg gggcgcagcc gctgcccttc cccggcatgg acaagtcggg cgctgctgtc    120
tgtgaattct ttttgaaagc tgcctgcggc aaaggggca tgtgtccgtt tcgccacatc     180
agtggtgaga agacagttgt gtgcaaacac tggctgcgtg gcctatgcaa gaaaggggac    240
cagtgtgagt tcctgcatga gtatgacatg accaagatgc ccgagtgcta cttctactcc    300
aagttcgggg agtgcagcaa caaggaatgt cccttcctgc acatcgaccc cgagtccaag    360
atcaaggact gtccttggta tgaccgtggc ttctgcaagc acggtcccct ctgcaggcac    420
cggcacacac ggagagtcat ctgtgtgaat tacctcgtgg gattctgccc ggaggggccc    480
tcgtgtaaat tcatgcaccc tcgatttgaa ctgcccatgg aaccaccga gcagccccca    540 ctgccgcagc agacacagcc tccagcaaag caaagtaaca atccgccatt acaaaggtcg    600
tcctccttga tccagttaac gagtcagaac tcttctccca atcagcagag aacccgcag    660 gtcatcgggg tcatgcagag tcaaaacagc agcgcgggca accggggacc ccggccactg    720
gagcaggtca cctgttacaa gtgtggcgag aaaggacact acgccaacag atgcaccaaa    780
gggcacttgg cctttctcag tggacagtga tga                                813
```

<210> SEQ ID NO 2
<211> LENGTH: 269
<212> TYPE: PRT
<213> ORGANISM: Homo sapiens

<400> SEQUENCE: 2

Met Gln Glu Ile Ile Ala Ser Val Asp His Ile Lys Phe Asp Leu Glu
1               5                   10                  15

Ile Ala Val Glu Gln Gln Leu Gly Ala Gln Pro Leu Pro Phe Pro Gly
            20                  25                  30

Met Asp Lys Ser Gly Ala Ala Val Cys Glu Phe Phe Leu Lys Ala Ala
        35                  40                  45

Cys Gly Lys Gly Gly Met Cys Pro Phe Arg His Ile Ser Gly Glu Lys
    50                  55                  60

Thr Val Val Cys Lys His Trp Leu Arg Gly Leu Cys Lys Lys Gly Asp
65                  70                  75                  80

Gln Cys Glu Phe Leu His Glu Tyr Asp Met Thr Lys Met Pro Glu Cys
                85                  90                  95

Tyr Phe Tyr Ser Lys Phe Gly Glu Cys Ser Asn Lys Glu Cys Pro Phe
            100                 105                 110

Leu His Ile Asp Pro Glu Ser Lys Ile Lys Asp Cys Pro Trp Tyr Asp
        115                 120                 125

Arg Gly Phe Cys Lys His Gly Pro Leu Cys Arg His Arg His Thr Arg
    130                 135                 140

Arg Val Ile Cys Val Asn Tyr Leu Val Gly Phe Cys Pro Glu Gly Pro
145                 150                 155                 160

Ser Cys Lys Phe Met His Pro Arg Phe Glu Leu Pro Met Gly Thr Thr
                165                 170                 175

Glu Gln Pro Pro Leu Pro Gln Gln Thr Gln Pro Ala Lys Gln Ser
            180                 185                 190

Asn Asn Pro Pro Leu Gln Arg Ser Ser Leu Ile Gln Leu Thr Ser
            195                 200                 205

Gln Asn Ser Ser Pro Asn Gln Gln Arg Thr Pro Gln Val Ile Gly Val
    210                 215                 220

Met Gln Ser Gln Asn Ser Ser Ala Gly Asn Arg Gly Pro Arg Pro Leu
225                 230                 235                 240

Glu Gln Val Thr Cys Tyr Lys Cys Gly Glu Lys Gly His Tyr Ala Asn
                245                 250                 255

Arg Cys Thr Lys Gly His Leu Ala Phe Leu Ser Gly Gln
            260                 265

<210> SEQ ID NO 3
<211> LENGTH: 27
<212> TYPE: PRT
<213> ORGANISM: Homo sapiens

<400> SEQUENCE: 3

Asp Lys Ser Gly Ala Ala Val Cys Glu Phe Phe Leu Lys Ala Ala Cys
1               5                   10                  15

Gly Lys Gly Gly Met Cys Pro Phe Arg His Ile
            20                  25

<210> SEQ ID NO 4
<211> LENGTH: 30
<212> TYPE: PRT
<213> ORGANISM: Homo sapiens

-continued

```
<400> SEQUENCE: 4

Ser Gly Glu Lys Thr Val Val Cys Lys His Trp Leu Arg Gly Leu Cys
1               5                   10                  15

Lys Lys Gly Asp Gln Cys Glu Phe Leu His Glu Tyr Asp Met
            20                  25                  30

<210> SEQ ID NO 5
<211> LENGTH: 31
<212> TYPE: PRT
<213> ORGANISM: Homo sapiens

<400> SEQUENCE: 5

Thr Lys Met Pro Glu Cys Tyr Phe Tyr Ser Lys Phe Gly Glu Cys Ser
1               5                   10                  15

Asn Lys Glu Cys Pro Phe Leu His Ile Asp Pro Glu Ser Lys Ile
            20                  25                  30

<210> SEQ ID NO 6
<211> LENGTH: 24
<212> TYPE: PRT
<213> ORGANISM: Homo sapiens

<400> SEQUENCE: 6

Lys Asp Cys Pro Trp Tyr Asp Arg Gly Phe Cys Lys His Gly Pro Leu
1               5                   10                  15

Cys Arg His Arg His Thr Arg Arg
            20

<210> SEQ ID NO 7
<211> LENGTH: 61
<212> TYPE: PRT
<213> ORGANISM: Homo sapiens

<400> SEQUENCE: 7

Ser Gly Glu Lys Thr Val Val Cys Lys His Trp Leu Arg Gly Leu Cys
1               5                   10                  15

Lys Lys Gly Asp Gln Cys Glu Phe Leu His Glu Tyr Asp Met Thr Lys
            20                  25                  30

Met Pro Glu Cys Tyr Phe Tyr Ser Lys Phe Gly Glu Cys Ser Asn Lys
        35                  40                  45

Glu Cys Pro Phe Leu His Ile Asp Pro Glu Ser Lys Ile
    50                  55                  60

<210> SEQ ID NO 8
<211> LENGTH: 145
<212> TYPE: PRT
<213> ORGANISM: Homo sapiens

<400> SEQUENCE: 8

Met Gln Glu Val Ile Ala Gly Leu Glu Arg Phe Thr Phe Ala Phe Glu
1               5                   10                  15

Lys Asp Val Glu Met Gln Lys Gly Thr Gly Leu Leu Pro Phe Gln Gly
            20                  25                  30

Met Asp Lys Ser Ala Ser Ala Val Cys Asn Phe Phe Thr Lys Gly Leu
        35                  40                  45

Cys Glu Lys Gly Lys Leu Cys Pro Phe Arg His Asp Arg Gly Glu Lys
    50                  55                  60

Met Val Val Cys Lys His Trp Leu Arg Gly Leu Cys Lys Lys Gly Asp
65                  70                  75                  80
```

His Cys Lys Phe Leu His Gln Tyr Asp Leu Thr Arg Met Pro Glu Cys
                85                  90                  95

Tyr Phe Tyr Ser Lys Phe Asp Lys Gln Lys Cys Thr Leu Lys Ser Leu
            100                 105                 110

Pro Phe Thr Ala Pro Trp Ile Lys Pro Ala Ser Gly Pro Pro Lys Arg
        115                 120                 125

Leu Leu Leu Ile Ser Ala Asn Gly Arg Val Leu Gly Asp Cys Ser Asn
    130                 135                 140

Lys
145

<210> SEQ ID NO 9
<211> LENGTH: 121
<212> TYPE: PRT
<213> ORGANISM: Homo sapiens

<400> SEQUENCE: 9

Met Gln Glu Val Ile Ala Gly Leu Glu Arg Phe Thr Phe Ala Phe Glu
1               5                   10                  15

Lys Asp Val Glu Met Gln Lys Gly Thr Gly Leu Leu Pro Phe Gln Gly
            20                  25                  30

Met Asp Lys Ser Ala Ser Ala Val Cys Asn Phe Phe Thr Lys Gly Leu
        35                  40                  45

Cys Glu Lys Gly Lys Leu Cys Pro Phe Arg His Asp Arg Gly Glu Lys
    50                  55                  60

Met Val Val Cys Lys His Trp Leu Arg Gly Leu Cys Lys Lys Gly Asp
65                  70                  75                  80

His Cys Lys Phe Leu His Gln Tyr Asp Leu Thr Arg Met Pro Glu Cys
                85                  90                  95

Tyr Phe Tyr Ser Lys Phe Asp Lys Gln Lys Cys Thr Leu Lys Ser Leu
            100                 105                 110

Pro Phe Thr Ala Pro Trp Ile Lys Pro
        115                 120

<210> SEQ ID NO 10
<211> LENGTH: 92
<212> TYPE: PRT
<213> ORGANISM: Homo sapiens

<400> SEQUENCE: 10

Met Gln Glu Val Ile Ala Gly Leu Glu Arg Phe Thr Phe Ala Phe Glu
1               5                   10                  15

Lys Asp Val Glu Met Gln Lys Gly Thr Gly Leu Leu Pro Phe Gln Gly
            20                  25                  30

Met Asp Lys Ser Ala Ser Ala Val Cys Asn Phe Phe Thr Lys Gly Leu
        35                  40                  45

Cys Glu Lys Gly Lys Leu Cys Pro Phe Arg His Asp Arg Gly Glu Lys
    50                  55                  60

Met Val Val Cys Lys His Trp Leu Arg Gly Leu Cys Lys Lys Gly Asp
65                  70                  75                  80

His Cys Lys Phe Leu His Gln Tyr Asp Leu Thr Arg
                85                  90

<210> SEQ ID NO 11
<211> LENGTH: 88
<212> TYPE: PRT
<213> ORGANISM: Homo sapiens

```
<400> SEQUENCE: 11

Asp Lys Ser Ala Ser Ala Val Cys Asn Phe Phe Thr Lys Gly Leu Cys
1               5                   10                  15

Glu Lys Gly Lys Leu Cys Pro Phe Arg His Asp Arg Gly Glu Lys Met
            20                  25                  30

Val Val Cys Lys His Trp Leu Arg Gly Leu Cys Lys Lys Gly Asp His
        35                  40                  45

Cys Lys Phe Leu His Gln Tyr Asp Leu Thr Arg Met Pro Glu Cys Tyr
    50                  55                  60

Phe Tyr Ser Lys Phe Asp Lys Gln Lys Cys Thr Leu Lys Ser Leu Pro
65                  70                  75                  80

Phe Thr Ala Pro Trp Ile Lys Pro
                85

<210> SEQ ID NO 12
<211> LENGTH: 61
<212> TYPE: PRT
<213> ORGANISM: Homo sapiens

<400> SEQUENCE: 12

Arg Gly Glu Lys Met Val Val Cys Lys His Trp Leu Arg Gly Leu Cys
1               5                   10                  15

Lys Lys Gly Asp His Cys Lys Phe Leu His Gln Tyr Asp Leu Thr Arg
            20                  25                  30

Met Pro Glu Cys Tyr Phe Tyr Ser Lys Phe Asp Lys Gln Lys Cys Thr
        35                  40                  45

Leu Lys Ser Leu Pro Phe Thr Ala Pro Trp Ile Lys Pro
    50                  55                  60

<210> SEQ ID NO 13
<211> LENGTH: 9
<212> TYPE: PRT
<213> ORGANISM: Artificial Sequence
<220> FEATURE:
<223> OTHER INFORMATION: SV40 T antigen NLS

<400> SEQUENCE: 13

Asp Pro Lys Lys Lys Arg Lys Val
1               5

<210> SEQ ID NO 14
<211> LENGTH: 10
<212> TYPE: PRT
<213> ORGANISM: Artificial Sequence
<220> FEATURE:
<223> OTHER INFORMATION: Myc epitope

<400> SEQUENCE: 14

Glu Gln Lys Leu Ile Ser Glu Glu Asp Leu
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Mutant 144

<400> SEQUENCE: 15

Leu Glu Thr Leu Ile Leu Leu
1               5
```

DEVELOPMENT OF INFLUENZA A ANTIVIRALS

CROSS-REFERENCE TO RELATED APPLICATIONS

This application claims priority to U.S. Provisional Application Ser. No. 60/741,764, filed Dec. 2, 2005; and Ser. No. 60/852,361 filed Oct. 16, 2006, the entire contents of which are incorporated herein by reference. This application is related to U.S. patent application Ser. No. 11/566,214, also filed on Dec. 2, 2006, now U.S. Pat. No. 7,601,490 issued Oct. 13, 2009.

STATEMENT OF FEDERALLY FUNDED RESEARCH

This invention was made with U.S. Government support under Public Health Service grant AI-11772 from the National Institutes of Health. The government has certain rights in this invention.

TECHNICAL FIELD OF THE INVENTION

The present invention relates in general to the field of antiviral agents, and more particularly, novel antiviral agents with the F2F3 zinc fingers of a cleavage and polyadenylation specificity factor 30 KDa subunit (CPSF30) protein and an Influenza A NS 1A protein; and determining whether the binding between the CPSF30 protein and the Influenza A NS1A protein is reduced.

BACKGROUND OF THE INVENTION

Without limiting the scope of the invention, its background is described in connection with antiviral agents.

Influenza A viruses cause a highly contagious respiratory disease in humans that results in a significant loss of life each year, and are responsible for human pandemics that have resulted in higher mortality rates (2). Three pandemics occurred in the twentieth century, in 1918, 1957 and 1968 (23). The 1918 pandemic ("Spanish flu") was the most devastating, causing at least 20-40 million deaths worldwide (19). H5N1 avian influenza A viruses, which have a human mortality rate of approximately 50% since 1997 (22), are prime candidates for the next pandemic influenza A virus. At present, H5N1 viruses are not readily transmissible between humans, but it is quite possible that they can acquire such transmissibility via mutations and/or reassortment of genes with circulating human influenza A viruses.

The primary way of controlling influenza virus epidemics is vaccination, but antivirals provide an important additional line of defense, particularly for a rapidly-spreading pandemic (5, 11). Only two classes of influenza virus antivirals are currently available: inhibitors of the viral M2 ion channel protein (amantadine and rimantadine); and inhibitors of the viral neuraminidase (zanamivir and oseltamivir) (reviewed in 23). The emergence of influenza A viruses resistant to the M2 inhibitors occurs at high frequency in treated patients (4, 21). Many of the human isolates of H5N1 viruses are already resistant to these inhibitors (17). In addition, a recent study has shown influenza A viruses resistant to the neuraminidase inhibitor oseltamivir occurred in 20% of the children treated with this drug (8). In fact, H5N1 viruses that are partially resistant to oseltamivir have recently been reported (9). The emergence of influenza A viruses resistant to these two classes of antiviral drugs highlights the need for additional antiviral drugs against influenza A virus. Therefore, a need exists for novel antiviral agents that address one or more locations in the viral replication cycle.

SUMMARY OF THE INVENTION

The present inventors have developed compositions, methods and systems for the isolation, characterization and development of new antiviral agents that affect influenza A virus replication. The compositions of the present invention were able to selectively inhibit Influenza A replication by blocking the ability of its NS1A protein to inhibit the 3' end processing of cellular pre-mRNAs, including interferon-β (IFN-β) pre-mRNA. Pre-mRNA processing was inhibited via the binding of the NS1A protein to the cellular CPSF30 protein, and mutational inactivation of this NS1A binding site causes severe attenuation of the virus.

In addition to the compositions and methods disclosed herein, small chemical compounds that bind strongly and specifically to the NS1A protein at its CPSF30 binding site will be effective inhibitors of influenza A virus replication. The concentration of such small chemical compounds that can be achieved in cells will greatly exceed the concentration of the F2F3 fragment achieved in the present study, resulting in a reduction of virus yield similar to that observed with mutational inactivation of the CPSF30 binding site on the NS1A protein.

Further, the lack of any apparent growth impediment of the F2F3-expressing cells during two years in tissue culture may be used for the identification of small chemical compounds that bind with high specificity to the CPSF30 binding site on the NS1A protein without affecting the 3' end processing of host cell pre-mRNAs. It should be pointed out that the present study has already suggested an assay for the identification of such small molecule inhibitors of influenza A virus replication, specifically, a high-throughput assay to identify small chemical compounds that inhibit the binding of the F2F3 fragment to the NS1A protein. Small chemical compounds directed against the CPSF30 binding site of the NS1A protein would be expected to inhibit the replication of all strains of influenza A virus.

It was also found that the binding of the Influenza A NS1A protein to CPSF30 is mediated by two of its zinc fingers, F2F3, and that the CPSF30/F2F3 binding site on the NS1A protein includes the region between amino acids 144 and 186. MDCK cells were generated that constitutively express epitope-tagged F2F3 in the nucleus, although at only approximately one-eighth the level of the NS1A protein produced during virus infection. Influenza A virus replication was inhibited in this cell line, whereas no inhibition was observed with influenza B virus, whose NS1B protein lacks a binding site for CPSF30. Influenza A virus, but not influenza B virus, induced increased production of IFN-β mRNA in the F2F3-expressing cells. These results, which indicate that F2F3 inhibits influenza A virus replication by blocking the binding of endogenous CPSF30 to the NS1A protein, point to this NS1A binding site as a potential target for the development of antivirals directed against influenza A virus.

More particularly, the present invention includes compositions and methods of inhibiting Influenza A replication by expressing one or more F2F3 zinc fingers from the CPSF30 protein in a cell, wherein the zinc fingers bind with an Influenza A NS1A protein. Examples of strains that may be inhibited include, but are not limited to, H5N1, A/Udorn/72, A/WSN/33, B/Lee/40 or combinations thereof. In one embodiment, the F2F3 zinc fingers reduce production of interferon-α/β (IFN-α/β)-independent antiviral mRNAs by the Influenza A. To determine the extent of inhibition, the F2F3 zinc fingers may be used to prevent Influenza A NS1A protein-mediated reduction of an interferon-α, an interferon-β and combinations thereof. The zinc fingers and mutations thereof will be particularly useful if they do not inhibit 3' end processing of cellular pre-mRNAs. The F2F3 zinc fingers may also include non-CPSF30 protein amino acids, e.g., peptides. In one example, the F2F3 zinc fingers may include 1, 2, 5, 10, 13, 15 or more tags, e.g., myc tags or fusion protein partners, e.g., glutathione-S-transferase (GST). The F2F3 zinc fingers may be a GST-F2F3-13×myc.

The present invention also includes a method for identifying a candidate antiviral agent by contacting the antiviral agent with the F2F3 zinc fingers of an CPSF30 protein and an Influenza A NS1A protein; and determining whether the binding between the CPSF30 protein and the Influenza A NS1A protein is reduced. The method may also include the step of determining the binding between F2F3 zinc fingers and Influenza A NS1A protein by measuring the production of interferon-α/β (IFN-α/β)-independent antiviral mRNAs by the Influenza A. The step of determining the binding between F2F3 zinc fingers and Influenza A NS1A protein may include using a detectable marker on one or both the F2F3 zinc fingers and the Influenza A NS1A protein. The step of detecting the binding may even occur within a cell.

The present invention also include a vector that includes a nucleic acid segment encoding one or more F2F3 zinc fingers of the CPSF30 protein and/or host cell comprising a vector comprising a nucleic acid segment encoding one or more F2F3 zinc fingers of the CPSF30 protein.

In another embodiment, the present invention includes an antiviral composition comprising one or more isolated and purified F2F3 zinc fingers of the CPSF30 protein. Examples of useful variants of the F2F3 zinc fingers are those that bind specifically to the CPSF30 binding site of the NS1A protein, does not inhibit the 3' end processing of cellular pre-mRNAs or both. The variants and other antiviral agents may also be isolated and purified nucleic acids that includes one or more F2F3 zinc fingers of the CPSF30 protein and are delivered to a target cell using delivery vectors, e.g., viral, liposomal, etc. An isolated and purified CPSF30 protein is also included that has been mutated at zinc fingers F2F3 that blocks Influenza virus NS1A function without affecting cellular pre-mRNA processing.

Yet another embodiment of the present invention includes a method for identifying an antiviral agent for a human by selecting the antiviral agent based on its ability to prevent the interaction between one or more F2F3 zinc fingers of an CPSF30 protein and an Influenza A NS1A protein; and selecting the antiviral agent that has antiviral activity without an adverse effect on the human cell.

BRIEF DESCRIPTION OF THE DRAWINGS

For a more complete understanding of the features and advantages of the present invention, reference is now made to the detailed description of the invention along with the accompanying figures and in which:

FIG. 8. Proposed mechanism for the selective inhibition of influenza A virus replication by the F2F3 fragment of CPSF30.

DETAILED DESCRIPTION OF THE INVENTION

Figure 1:
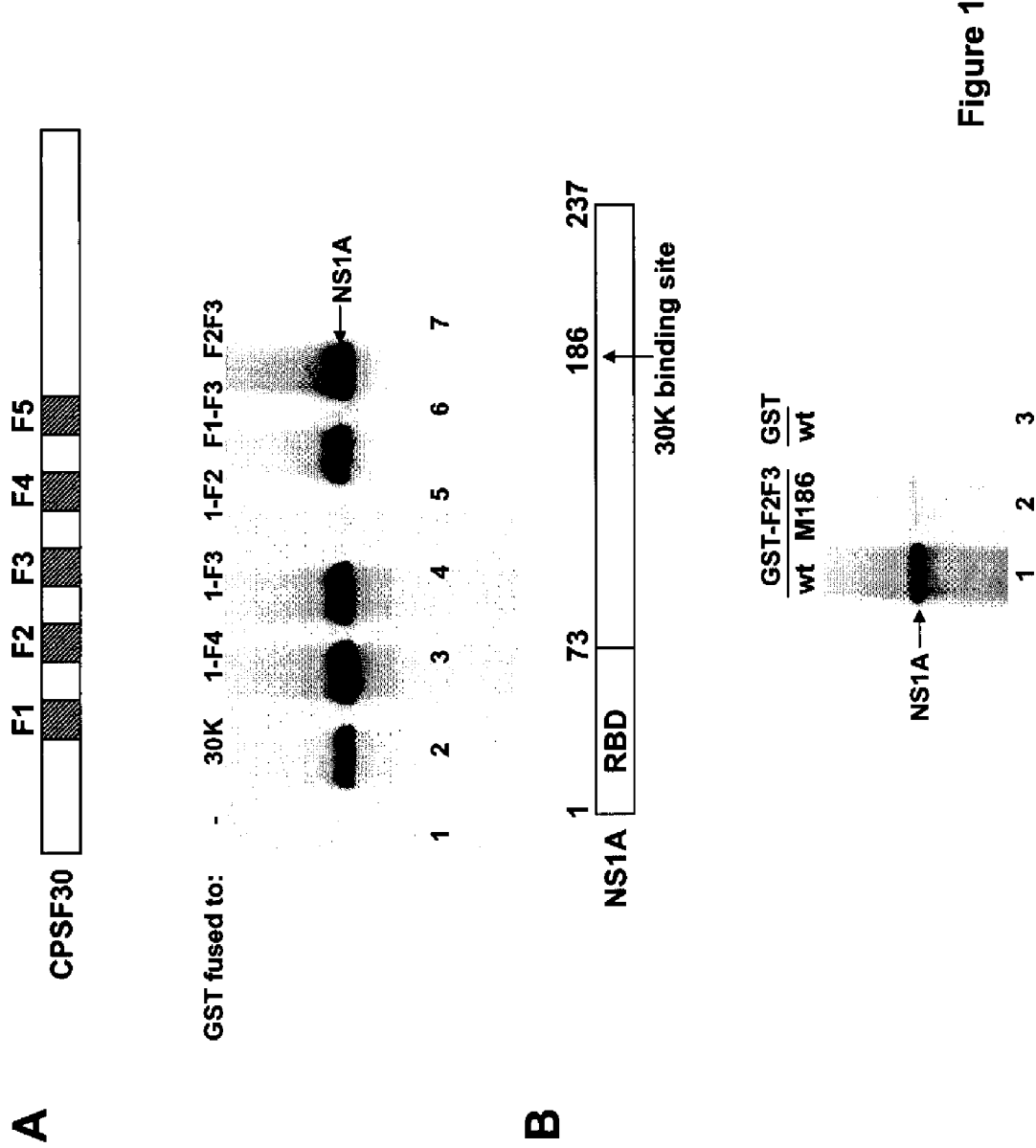
FIG. 1. Identification of the region of CPSF30 that binds to the 186 amino acid region of the NS1A protein. (A) GST fusions containing the indicated regions of CPSF30 were mixed with $^{35}$S-labeled wt NS1A protein, followed by affinity chromatography on Glutathione-Sepharose. (B) GST-F2F3 or GST was mixed with $^{35}$S-labeled wt or M186 mutant NS1A protein as indicated, followed by affinity chromatography on Glutathione-Sepharose.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "Influenza A" is intended to include mammalian Influenza A virus, e.g., H3N2, H1N1, H2N2, H7N7 and H5N1 (avian influenza virus) strains and variants thereof.

As used herein, the phrase "anti-viral peptide" refers to an amino acid chain (peptide or polypeptide) that inhibits viral growth and/or proliferation, or to reduce the infectivity of a virus particle or population. An "effective amount of an anti-viral agent" refers to an amount, or dose, within the range normally given or prescribed to demonstrate an anti-viral effect, e.g., in vitro or in vivo. The range of an effective amount may vary from individual to individual, however, the optimal dose is readily determinable by those of skill in the art depending upon the use to which the peptide is to be applied. Such ranges are well established in routine clinical practice and will thus be readily determinable to those of skill in the art. Doses may be measured by total amount given or by concentration. Doses of 0.01, 0.05, 0.1, 0.5, 1, 2, 3, 4, 5, 6, 7, 8, 9, 10, 15, 20, 25, 30, 40, 50, 100, 500 and 1000 μg/ml solutions all are appropriate for treatment.

The present invention may be used alone or in combination with other anti-viral agents such that the effective amounts of a second anti-viral agent may be used that are lower than the standard doses previously recommended, when the second anti-viral is combined with an anti-viral peptide. The anti-viral peptide may be used in combination with these other anti-viral agents for a variety of purposes, e.g., to allow the use of a lower dose of the anti-viral due to toxicity or dosing concerns relating to the second agent, enhancing the activity of anti-viral agents against strains that have previously exhibited resistance to an anti-viral agent, or providing an additional anti-viral agent in individuals whose immune system is damaged or compromised and are thus unable to mount an effective immune response.

Where a combination of an anti-viral peptide and one or more conventional anti-viral agents is contemplated, it is envisioned that the anti-viral peptide and the second anti-viral agent may be delivered either simultaneously or either of the agents may be administered prior to the administration of the other. Staggered administration of the agents may also might reduce the infectivity or number of viruses and increase the efficacy of the additional agent.

The term "gene" is used to refer to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "vector" is used in reference to nucleic acid molecules that transfer DNA segment(s) from one cell to another. The vector may be further defined as one designed to propagate specific sequences, or as an expression vector that includes a promoter operatively linked to the specific sequence, or one designed to cause such a promoter to be introduced. The vector may exist in a state independent of the host cell chromosome, or may be integrated into the host cell chromosome.

The term "host cell" refers to cells that have been engineered to contain nucleic acid segments or altered segments, whether archeal, prokaryotic, or eukaryotic. Thus, engineered, or recombinant cells, are distinguishable from naturally occurring cells that do not contain recombinantly introduced genes.

As used herein, the term "aptamer" refers to an oligonucleotide that has been designed or discovered that is able to specifically bind a target sequence. As used herein, the term "allosteric effector" or "allosteric effector molecule" are used to describe a substance that allosterically changes the kinetic parameters or binding activity of the interaction between CPSF30 protein and the Influenza A NS1A protein in vivo and/or in vitro. As used herein the terms "protein", "polypeptide" or "peptide" refer to compounds comprising amino acids joined via peptide bonds and are used interchangeably.

As used herein, the terms "vaccinating," "vaccination," "vaccine," "immunizing," "immunization," refer to the process of preparing the immune system of a patient to respond to an antigen of an agent. Passive immunity refers to the transfer of antigen-specific immunoglobulins or cells that are specific for an antigen to a patient that has not been exposed to the antigen, is unable to elicit an immune response to the antigen or to boost the host immune response to an antigen. Vaccination may include both prophylactic and therapeutic vaccines.

The present invention includes compositions and methods for identifying new agents that act to inhibit the interaction between CPSF30 protein and the Influenza A NS1A protein, and that may be termed as "candidate substances." It is contemplated that this screening technique will prove useful in the general identification of any compound that will serve the purpose of inhibiting the interaction of the F2F3 zinc fingers of CPSF30 and the Influenza A NS1A. It is further contemplated that useful compounds in this regard may include aptamers, peptide and small molecular agents, pools of agents or extracts (purified or partially purified) that physically or allosterically inhibit this interaction. In fact, it may prove to be the case that the most useful pharmacological compounds for identification through application of the screening assay will be non-peptidyl in nature and serve to inactivate the interaction through a tight binding or other chemical interaction.

When designing alternate peptide constructs with enhanced anti-viral properties, substitutions may be used which modulate one or more properties of the molecule. Variants typically include the exchange of one amino acid for another at one or more sites within the peptide. For example, certain amino acids may be substituted for other amino acids in a peptide structure in order to enhance the interactive binding capacity of the structures. Certain amino acid substitutions can be made in a protein sequence (or its underlying DNA coding sequence) to create a peptide with superior functional characteristics. In particular, those changes that enhance the amphipathic, α-helical nature may be desired.

One variable for selecting amino acid substitutions is the hydropathic index of amino acids. The importance of the hydropathic amino acid index in conferring interactive biologic function on a protein is generally understood in the art (Kyte & Doolittle, 1982). The relative hydropathic character of the amino acid contributes to the secondary structure of the resultant protein, which in turn defines the interaction of the protein with other molecules. For example, each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within +/−2 are often used, as are those within +1, as well and those within +/−0.5.

The substitution of amino acids can be made effectively on the basis of hydrophilicity. U.S. Pat. No. 4,554,101, relevant portions incorporated herein by reference, teaches that the greatest local average hydrophilicity of a protein, as governed by the hydrophilicity of its adjacent amino acids, correlates with a biological property of the protein. The following hydrophilicity values have been assigned to amino acid residues and may be used as guidelines for amino acid substitutions: arginine (+3.0); lysine (+3.0); aspartate (+3.0.+-0.1); glutamate (+3.0.+-0.1); serine (+0.3); asparagine (+0.2); glutamine (+0.2); glycine (0); threonine (−0.4); proline (−0.5.+-0.1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

Amino acid substitutions are based generally on the relative similarity of the amino acid side-chain substituents, for example, their hydrophobicity, hydrophilicity, charge, size and the like. Exemplary substitutions that take advantage of the foregoing characteristics into consideration are well known to those of skill in the art and include, e.g., arginine and lysine; glutamate and aspartate; serine and threonine; glutamine and asparagine; and valine, leucine and isoleucine.

Anti-viral peptides may also be made at the genetic level by, e.g., cloning and expression. Fusion proteins may be made that incorporate one or more peptides (e.g., peptide concatamers that include cleavage sides between peptide segments) at the nucleic acid sequence that encode and express one or more anti-viral peptides alone or with a desired fusion partner. The anti-viral peptide sequences may be made in vitro or from artificial or natural DNAs. Such sequences may be prepared synthetically, but also through conventional techniques using probes to recover corresponding DNAs from genomic or cDNA libraries. Following cloning, such DNAs can then be incorporated in appropriate expression vectors and used to transform host cells (e.g., bacterial or mammalian cells), which can be cultured to form recombinant anti-viral peptides.

The anti-viral peptides (and/or second agents) may be formulated and administered in any pharmacologically acceptable vehicle, such as parenteral, topical, aerosal, liposomal, nasal or ophthalmic preparations, with formulations designed for oral administration being currently preferred due to their ease of use. The anti-viral peptides may be formulated and administered in a manner that does not require that they be coupled with a pharmaceutically acceptable carrier. In those situations, it would be clear to one of ordinary skill in the art the types of diluents that would be proper for the proposed use of the peptides and any secondary agents required. Although further purification following synthesis may be desired, it is not necessarily required for use.

The anti-viral peptides may be used as a decontaminating agent, e.g., formulated as a spray in a liquid or powdered form onto a surface or area that has contacted, or may come into contact with, a virus particle. The anti-viral decontaminating agent may be used in epidemics where rooms, buildings or outdoor areas may be treated. Similarly, if viruses are used as a biological warfare agent, equipment and troops may be treated by spraying, immersion, or swabbing. In addition, it also is possible to coat surfaces (e.g., protective suits or coverings, medical instruments) with peptides of the present invention.

Peptide purification techniques are well known to those of skill in the art, from crude fractionation of the cellular milieu to chemically-synthesized polypeptides. The anti-viral polypeptides may be purified using chromatographic, immunologic and electrophoretic techniques to achieve partial or complete purification (e.g., purification to homogeneity). Analytical methods for evaluating the anti-viral peptides include, e.g., ion-exchange chromatography, exclusion chromatography; polyacrylamide gel electrophoresis; isoelectric focusing.

As used herein, the term "purified peptide" refers to a composition, isolatable from other components, wherein the peptide is purified to any degree relative to its naturally-obtainable state. A purified peptide therefore also refers to a peptide, free from the environment in which it may naturally occur. Generally, "purified" refers to a peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more peptides in the composition. The term "purified to homogeneity" is used to mean that the composition has been purified such that there is single protein species based on the particular test of purity employed for example SDS-PAGE or HPLC.

There is no general requirement that the peptide always be provided in its most purified state. Less substantially purified products may be used depending on the target for treatment. Partial purification may be accomplished by using fewer purification steps in combination, or by using different forms of the same general purification scheme. For example, it is appreciated that a ion-exchange column chromatography performed using a high performance liquid chromatography (HPLC) apparatus will generally result in a greater purification than the same technique using a low pressure chromatography system. Methods exhibiting a lower degree of relative purification may have advantages in total recovery of protein product, or in maintaining the activity of an expressed protein. The migration of a peptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. Separation is achieved by the use of very fine particles and high pressure to maintain an adequate flow rate and can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

For large volumes, affinity chromatography takes advantage of specific affinity between a substance to be isolated and a molecule to which it will specifically bind. A target-specific column material is synthesized by coupling covalently one of the binding partners to an insoluble matrix. The column material is then able to specifically adsorb the substance from the solution. Elution occurs by changing the conditions to those in which binding will not occur (alter pH, ionic strength, temperature, etc.). The target-specific column material is bound to a matrix that does not adsorb molecules to any significant extent and that has a broad range of chemical, physical and thermal stability. The ligand should be coupled in such a way as to not affect its binding properties. The ligand should also provide relatively tight binding and should permit elution of the target substance without destroying its activity. One of the most common forms of affinity chromatography is immunoaffinity chromatography. The generation of antibodies that would be suitable for use in accord with the present invention is discussed below.

The anti-viral agents disclosed herein may be used in conjunction with methods to reduce virus growth, infectivity, burden, shed, development of anti-viral resistance, and to enhance the efficacy of traditional anti-viral therapies.

The anti-viral properties of the peptides disclosed herein allow them to be included in formulations to inhibit virus growth and proliferation. The purified anti-viral peptides may be used without further modifications or they may be diluted in a pharmaceutically acceptable carrier. The invention may be administered to humans or animals, included in food and pharmaceutical preparations. They anti-viral agents may also be used in medicinal and pharmaceutical products (such as fluid containers, iv. bags, tubing, syringes, etc.), as well as in cosmetic products, hygienic products, cleaning products and cleaning agents, as well as any material to which the peptides could be sprayed on or adhered to wherein the inhibition of virucidal growth on such a material is desired.

The dosage of an anti-viral peptide necessary to prevent viral growth and proliferation depends upon a number of factors including the types of virus that might be present, the environment into which the peptide is being introduced, and the time that the peptide is envisioned to remain in a given area.

As used herein, the phrases "pharmaceutically" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active antiviral agents of the present invention may be formulated into classic pharmaceutical preparations and administered via any common route so long as the target tissue is available via that route. These routes of administration include, e.g., oral, alveolar, nasal, buccal, rectal, vaginal or topical. In particular, use of the anti-viral peptides of the present invention in a condom or diaphragm, optionally in conjunction with a spermicidal or other contraceptive substance, is envisioned. Alternatively, administration may be orthotopic, intradermal, subcutaneous, intramuscular, intraperitoneal or intravenous. The antiviral agent may also be administered parenterally or intraperitoneally. Solutions of the antiviral agent may be compounded into a free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The antiviral agent(s) will generally be provided in a pharmaceutical dosage form suitable for injectable use, e.g., sterile aqueous solutions or dispersions and sterile powders for the extemporaneous preparation of sterile injectable solutions or dispersions. For widespread use, the antiviral agents may be stable under the conditions of manufacture and storage and must be preserved against the contaminating action of microorganisms, such as bacteria and fungi. The antiviral agents will commonly be provided with a carrier, e.g., a solvent or dispersion medium that may include, e.g., water, ethanol, polyol (for example, glycerol, propylene glycol, and liquid polyethylene glycol, and the like), suitable mixtures thereof, and vegetable oils. Proper dosage fluidity can be maintained, for example, by the use of a coating, such as lecithin, by the maintenance of the required particle size in the case of dispersion and by the use of surfactants. The prevention of the action of microorganisms can be brought about by various antibacterial and/or antifungal agents, for example, parabens, chlorobutanol, phenol, sorbic acid, thimerosal, and the like. In many cases, the dosage form will include isotonic agents, e.g., sugars or sodium chloride. Prolonged absorption of the injectable compositions can be brought about by the use in the compositions of agents delaying absorption, for example, aluminum monostearate and gelatin.

Generally, sterile injectable solutions are prepared by incorporating the active compounds in the required amount in the appropriate solvent with various of the other ingredients enumerated above, as required, followed by sterilization. Generally, dispersions are prepared by incorporating the various sterilized active ingredients into a sterile vehicle that includes the basic dispersion medium and the required other ingredients from those enumerated above. Preparation of sterile powders for injectable solutions maybe prepared by, e.g., vacuum-drying, spray-freezing, freeze-drying or other techniques that yield a powder of the active ingredient plus any additional desired ingredient from a previously sterile-filtered solution thereof.

As used herein, a "pharmaceutically acceptable carrier" refers to solvents, dispersion media, coatings, antibacterial and anti-fungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration, the antiviral agent(s) of the present invention may be incorporated with excipients and used in the form of ingestible or non-ingestible mouthwashes and dentifrices. A mouthwash may be prepared incorporating the active ingredient in the required amount in an appropriate solvent, such as a sodium borate solution (Dobell's Solution). Alternatively, the antiviral agent(s) may be incorporated into an antiseptic wash containing sodium borate, glycerin and potassium bicarbonate. The antiviral agent(s) may also be dispersed in dentifrices, e.g., gels, pastes, powders and slurries. The antiviral agent(s) may be added in a therapeutically effective amount to a paste dentifrice that may include water, binders, abrasives, flavoring agents, foaming agents, and humectants.

The antiviral agent(s) may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric and the like. Salts may also be formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, the antiviral agent(s) will be administered in a manner compatible with the dosage formulation and in such amount as is therapeutically effective. The formulations are easily administered in a variety of dosage forms such as injectable solutions, drug release capsules and the like. Sterile aqueous media that can be employed will be known to those of skill in the art in light of the present disclosure, e.g., Remington: The Science and Practice of Pharmacy, 21st Edition, Lippincott Williams & Wilkins (2005), relevant portions incorporated herein by reference. Some variation in dosage will necessarily occur depending on the condition of the subject being treated for which the skilled artisan will determine the appropriate dose for the individual subject. Moreover, for human administration, preparations should meet sterility, pyrogenicity, general safety and purity standards as required by FDA Office of Biologics standards.

Accordingly, in screening assays to identify pharmaceutical agents that disrupt Influenza A NS1A binding to wild-type CPSF30 it is proposed that compounds isolated from natural sources such as plants, animals or even sources such as marine, forest or soil samples, may be assayed for the presence of potentially useful pharmaceutical agents. It will be understood that the pharmaceutical agents to be screened could also be derived from chemical compositions or man-made compounds. In important aspects, the candidate substances may be peptides, proteins and concatamers thereof. The suspected agents could also include proteins and peptides, such as those derived from recombinant DNA technology or by other means, including peptide synthesis, e.g., an F2F3 zinc finger protein that is delivered to the cytoplasm be addition to one or more toxin subunits. The active compounds may include fragments or parts of naturally-occurring compounds or may be only found as active combinations of known compounds which are otherwise inactive.

Any method may generally be employed to determine NS1A binding to F2F3 binding. Such methods may include those that incorporate either the NS1A, F2F3, or both that are conjugated to, a label, such as an enzymatic, chemical or radiolabel, or incorporates one of the ligands of a two ligand-based detection system such as the avidin/biotin system. For ease and safety, the use of enzymatic labels, such as, for example, horse radish peroxidase, urease or alkaline phosphatase of fluorescence resonance energy transfer pairs (or a quencher).

The terms "a sequence essentially as set forth in SEQ ID NO. (#)", "a sequence similar to", "nucleotide sequence" and similar terms, with respect to nucleotides, refers to sequences that substantially correspond to any portion of the sequence identified herein as SEQ ID NO.: 1. These terms refer to synthetic as well as naturally-derived molecules and includes sequences that possess biologically, immunologically, experimentally, or otherwise functionally equivalent activity, for instance with respect to hybridization by nucleic acid segments, or the ability to encode all or portions of the F3F3 zinc fingers of CPSF30 or biologically equivalent activities with other viruses that inhibit interferons. Naturally, these terms are meant to include information in such a sequence as specified by its linear order.

The term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

Examples of "test compound(s)" for use with the present invention include new or known small molecules (or libraries of molecules) that may be used for the treatment of a mammal that inhibits any interaction between F2F3 and the Influenza A NS1A protein. In one example, the test compounds are already approved for another indication. A number of test compounds may be tested, isolated and purified using the methods of the present invention. Examples of known compounds or compound libraries that may be used with the present invention include, e.g., anti-virals, antitumor agents, anti-miotics, steroids, sympathomimetics, anesthetics, antimicrobials, antihypertensive agents, antihypertensive diuretics, cardiotonics, coronary vasodilators, vasoconstrictors, β-blockers, antiarrhythmic agents, calcium antagonists, anti-convulsants, agents for dizziness, tranquilizers, antipsychotics, muscle relaxants, respiratory agents, non-steroidal hormones, antihormones, vitamins, herb medicines, antimuscarinic, muscarinic cholinergic blocking agents, mydriatics, psychic energizers, humoral agents, antispasmodics, antidepressant drugs, anti-diabetics, anorectic drugs, anti-allergenics, decongestants, antipyretics, antimigrane, anti-malarials, anti-ulcerative, peptides, anti-estrogen, anti-hormone agents, antiulcer agents, anesthetic agent, drugs having an action on the central nervous system or combinations thereof. Additionally, one or more of the compounds may be combined with one or more carriers and the present invention (which may itself be the carrier).

Test compounds may be found and/or isolated from a variety of custom and commercially available combinatorial libraries. The compounds mentioned above may be used in combination as required. Moreover, the compounds may be used either in the free form or, if capable of forming salts, in the form of a salt with a suitable acid or base. If the drugs have a carboxyl group, their esters may be employed.

The present invention also includes pools and/or leads of therapeutic compounds in, e.g., a pharmaceutically acceptable carrier or diluent. With respect to in vivo applications, the compounds identified by screening methods may be administered to cells infected with Influenza A virus in a variety of ways including, for example, parenterally, orally or intraperitoneally. Parenteral administration includes administration by the following routes: intravenous, intramuscular, interstitial, intraperitoneal, intradural, epidural, intraarterial, subcutaneous, intraocular, intrasynovial, transepithelial, including transdermal, pulmonary via inhalation, opthalmic, sublingual and buccal, topical, including ophthalmic, dermal, ocular, rectal, vaginal and nasal inhalation via insufflation or nebulization.

The test compounds of this invention may be administered to a mammal alone or in combination with pharmaceutically acceptable carriers or as pharmaceutically acceptable salts, the proportion of which is determined by the solubility and chemical nature of the compound, chosen route of administration and standard pharmaceutical practice and even with other active agents, e.g., other antiviral agents. The compositions may also include other therapeutically active compounds that are usually applied in the treatment of the diseases and disorders, e.g., cancer. Treatments using active agents and other therapeutically active compounds may be administered simultaneously, in series, in parallel or by intervals.

The following nucleic acid sequence is the CPSF 30 kDa coding region (Accession No. NP—006684.1):

```
                                              SEQ ID NO.: 1
  1   atgcaggaaatcatcgccagcgtggaccacatcaagtttgactt
      ggagatcgcggtggag 61   cagcagctgggggcgcagccgctgcccttccccggcatggacaa
      gtcgggcgctgctgtc 121   tgtgaattcttttgaaagctgcctgcggcaaaggggcatgtg
      tccgtttcgccacatc 181   agtggtgagaagacagttgtgtgcaaacactggctgcgtggcct
      atgcaagaaggggac 241   cagtgtgagttcctgcatgagtatgacatgaccaagatgcccga
      gtgctacttctactcc 301   aagttcggggagtgcagcaacaaggaatgtcccttcctgcacat
      cgaccccgagtccaag 361   atcaaggactgtccttggtatgaccgtggcttctgcaagcacgg
      tccctctgcaggcac 421   cggcacacacggagagtcatctgtgtgaattacctcgtgggatt
      ctgcccggaggggccc 481   tcgtgtaaattcatgcaccctcgatttgaactgcccatgggaac
      caccgagcagccccca 541   ctgccgcagcagacacagcctccagcaaagcaaagtaacaatcc
      gccattacaaaggtcg 601   tcctccttgatccagttaacgagtcagaactcttctcccaatca
      gcagagaaccccgcag 661   gtcatcggggtcatgcagagtcaaaacagcagcgcgggcaaccg
      gggacccggccactg 721   gagcaggtcacctgttacaagtgtggcgagaaaggacactacgc
      caacagatgcaccaaa 781   gggcacttggcctttctcagtggacagtga
```

The following amino acid sequence is the CPSF 30 kDa protein (Accession No. NP—006684.1):

```
                                              SEQ ID NO.: 2
MQEIIASVDHIKFDLEIAVEQQLGAQPLPFPGMDKSGAAVCEFFLKAA

CGKGGMCPFRHISGEKTVVCKHWLRGLCKKGDQCEFLHEYDMTKMPEC

YFYSKFGECSNKECPFLHIDPESKIKDCPWYDRGFCKHGPLCRHRHTR

RVICVNYLVGFCPEGPSCKFMHPRFELPMGTTEQPPLPQQTQPPAKQS

NNPPLQRSSSLIQLTSQNSSPNQQRTPQVIGVMQSQNSSAGNRGPRPL

EQVTCYKCGEKGHYAMRCTKGHLAFLSGQ.
```

The F1 domain is amino acids 34-60 (SEQ ID NO. 3); F2 domain is amino acids 61-90 (SEQ ID NO. 4); F3 domain is amino acids 91-121 (SEQ ID NO. 5); F4 domain is amino acids 122-145 (SEQ ID NO. 6); and F2F3 domain is amino acids 61-121 (SEQ ID NO. 7).

The present invention was developed by determining whether one of the functions of the influenza A virus-encoded nonstructural protein, or NS1A protein, can be targeted for the development of antiviral drugs. NS1A protein-mediated inhibition of the 3' end processing of cellular pre-mRNAs results in the inhibition of the production of functional cellular mRNAs during infection (3, 14, 16, 20). As a consequence, the production of interferon-α/β (IFN-α/β)-independent antiviral mRNAs (e.g., ISG15, p56 and 2'-5'-oligo(A) synthetase mRNAs) is essentially eliminated, and the production of functional IFN-β mRNA is substantially reduced, although not eliminated (16). The NS1A protein inhibits the 3' end processing of cellular pre-mRNAs by binding two cellular proteins: the 30 kDa subunit of CPSF (cleavage and polyadenylation specificity factor) and PABII (poly(A)-binding protein II) (3, 14). The NS1A sequence centered at amino acid 186 is required for the binding of the 30 kDa subunit of CPSF (CPSF30), and mutation of this binding site renders the NS1A protein largely inactive in the inhibition of 3' end processing of cellular pre-mRNAs (10, 16).

The present inventors recognized that this binding site is also required for efficient virus replication, because a recombinant influenza A virus encoding a NS1A protein with a mutated 186 sequence (M186 mutant virus) is highly attenuated (16). This attenuation is most likely due to the enhanced production of functional cellular antiviral mRNAs, particularly IFN-β mRNA, that occurs in M186 virus-infected cells (16).

The present inventors discovered that the CPSF30 binding site of the NS1A protein is a potential target for the development of antivirals directed against influenza A virus. Specifically, molecules which block the binding of CPSF30 to this region of the NS1A protein might be expected to be effective inhibitors of virus replication. However, it is essential that such inhibitory molecules do not inhibit the function that CPSF30 carries out in the 3' end processing of cellular pre-mRNAs. In other words, these molecules would need to specifically block this viral NS1A function without affecting cellular pre-mRNA processing.

Using the present invention, it was found that the function of the CPSF30 binding site of the NS1A protein can be inhibited during influenza A virus infection in vivo, resulting in the inhibition of influenza A virus replication, without detectable effects on cellular functions. For these studies, a fragment of CPSF30 was used, specifically a 61-amino acid sequence comprising the second and third zinc fingers (F2F3) of this protein. It was found that the F2F3 fragment binds specifically and efficiently to the CPSF30 binding site of the NS1A protein, and does not inhibit the 3' end processing of cellular pre-mRNAs as measured in transient transfection studies. Most significantly, MDCK cells were generated that constitutively express epitope-tagged F2F3 in the nucleus, and demonstrate that influenza A virus replication is inhibited in these cells. In contrast, the replication of influenza B virus, whose NS1 protein (NS1B protein) lacks a CPSF30 binding site (16, 24), is not inhibited. Influenza A virus, but not influenza B virus, induced increased production of IFN-β mRNA in the F2F3-expressing cells compared to control cells, which is most likely responsible for the selective inhibition of influenza A virus replication. The F2F3-expressing cells have been maintained in tissue culture for two years, and we have not observed any effect on their growth. These results indicate that the CPSF30 binding site of the NS1A protein is a potential target for the development of small molecule antiviral drugs directed against influenza A virus.

Virus infections. For multiple cycle growth, MDCK cells were infected at a multiplicity of infection (moi) of 0.001 pfu/cell with either influenza A/Udorn/72, A/WSN/33 or B/Lee/40 virus, and were incubated in serum-free DMEM supplemented with 2.5 µg/ml of N-acetylated trypsin (NAT). Incubation was at 37° C. for the two influenza A viruses and at 34° C. for influenza B/Lee/40 virus. Maximal yields were obtained after 30-36 hours for the two influenza A viruses, and after 50-60 hours with influenza B virus. Plaque assays were carried out in MDCK cells. For the plaque reduction assays, monolayers of MDCK cells were infected with approximately 100 pfu of either influenza A/Udorn/72, influenza A/WSN/33, or influenza B/Lee/40 virus. After 1 hour of incubation at 37° C. or 34° C., the inoculum was removed, and the cells were overlaid with 1% agarose containing DMEM plus 2.5 µg/ml NAT. The cells were incubated for 3 days at 37° C. for the development of influenza A virus plaques, and for 4 days at 34° C. for influenza B/Lee/40 virus plaques. For single-cycle infections, MDCK cells were infected with 5 pfu/cell of either influenza A/Udorn/72 or influenza B/Lee/40 virus. After one hour incubation, the inoculum was removed, the cells were washed twice with DMEM, and then overlaid with DMEM.

Glutathione-Sepharose affinity selection. The DNAs encoding the following fragments of CPSF30 were generated by PCR using appropriate primers: 1-F4 (amino acids 1-145 (SEQ ID NO. 8); 1-F3 (amino acids 1-121 (SEQ ID NO. 9); 1-F2 (amino acids 1-92 (SEQ ID NO. 10); F1-F3 (amino acids 34-121 (SEQ ID NO. 11); F2F3 (amino acids 61-121 (SEQ ID NO. 12). These DNAs were then fused in frame (using PCR) into GST in the pGEX3X vector. Each GST fusion was expressed in E. coli. BL21, and purified as previously described (18). The indicated GST fusion protein was mixed with $^{35}$S-labeled NS1A protein (wild-type, M186 mutant, or M144 mutant), and subjected to Glutathione-Sepharose affinity selection as previously described (15). To prepare the labeled NS1A protein, the DNA encoding the indicated NS1A protein was subcloned into pcDNA3 and translated using a Promega TnT Coupled Transcription/Translation kit in the presence of ($^{35}$S) methionine.

Figure 2:
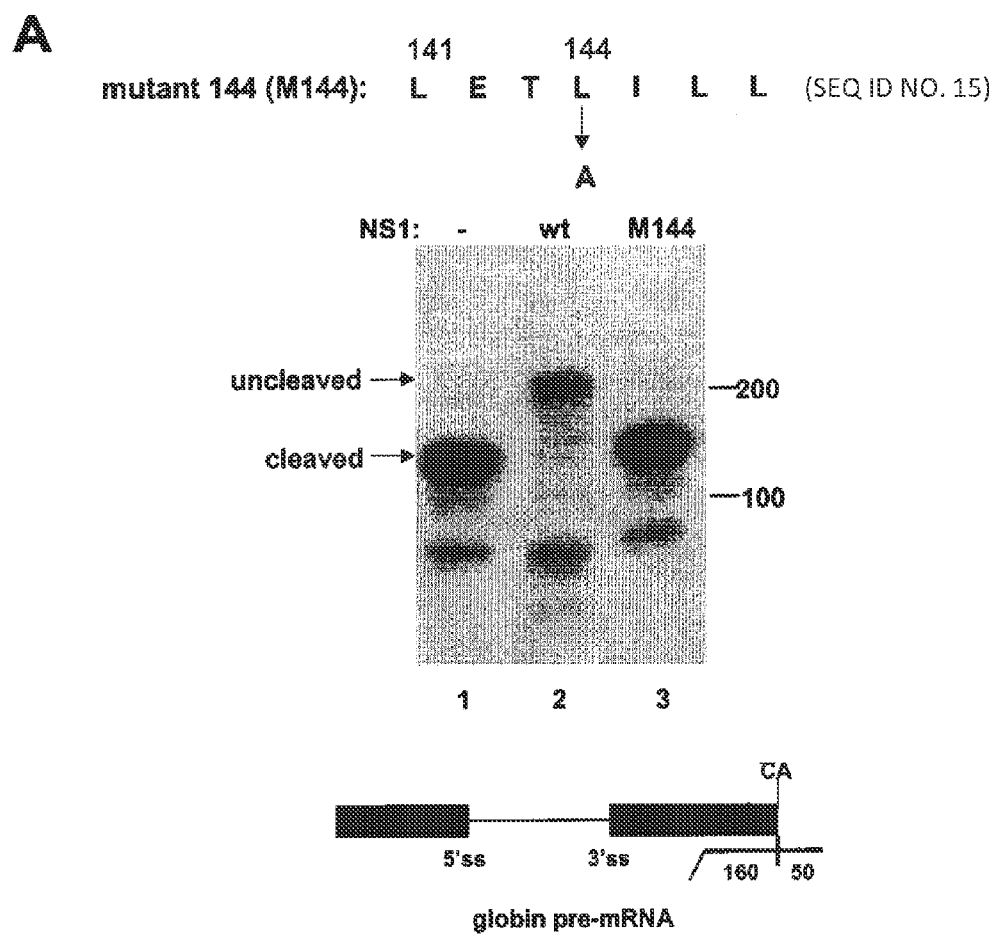
FIG. 2. The NS1A protein containing a L-to-A substitution at position 144 did not inhibit the 3' end processing of β-globin pre-mRNA and did not bind the F2F3 fragment of CPSF30. (A) 3' end processing assay. 293 cells were cotransfected with a pBC12 plasmid containing a human β-globin gene, and either an empty pcDNA3 plasmid (lane 1) or a pcDNA3 plasmid encoding wt NS1A protein (lane 2) or the M144 mutant NS1A protein (lane 3). The M144 sequence, which is diagramed above, was generated by RT-PCR using appropriate primers. RNA was analyzed by RNase protection using the indicated uniformly labeled RNA probe (270 nucleotides long). The protected RNA fragments were resolved by electrophoresis on a urea-polyacrylamide (5%) gel. The positions of the RNA fragments corresponding to the uncleaved and 3' end cleaved pre-mRNA are indicated. No residual probe containing 270 nucleotides was detected. (B) GST pulldown assay. GST-F2F3 or GST was mixed with $^{35}$S-labeled wt, M186 mutant, or M144 mutant NS1A protein as indicated, followed by affinity chromatography on Glutathione-Sepharose.
Figure 2:
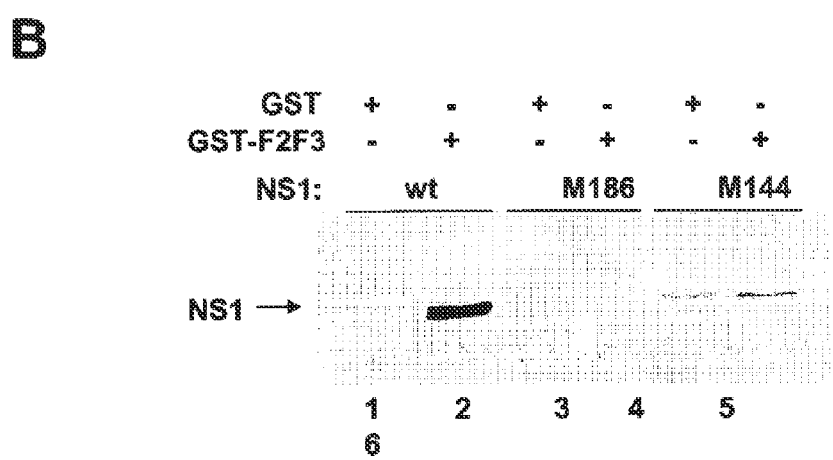
Figure 4:
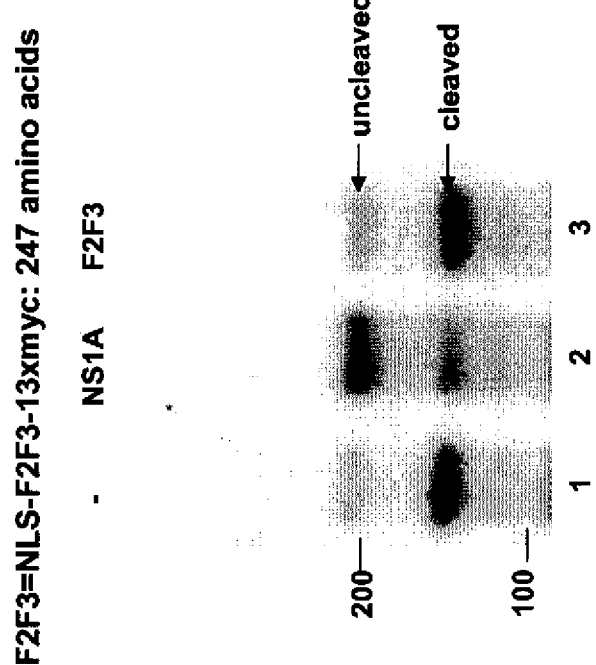
FIG. 4. Transient expression of the F2F3 protein fragment did not inhibit the 3' end processing of cellular pre-mRNAs. 293 cells were cotransfected with a pBC12 plasmid containing a human β-globin gene, and either an empty pcDNA3 plasmid (lane 1) or a pcDNA3 plasmid encoding wt NS1A protein (lane 2) or the F2F3 fragment (lane 3). The sequence of the F2F3 protein fragment is diagrammed above. Cells were collected 40 hours post-transfection, and RNA was analyzed by RNase protection as described in the legend of FIG. 2A. The positions of the RNA fragments corresponding to the uncleaved and 3' end cleaved pre-mRNA are indicated. No residual probe containing 270 nucleotides was detected.

Assay for 3' end cleavage of pre-mRNAs in vivo. 293 cells were cotransfected with a pBC12 plasmid containing a human β-globin gene, and a pcDNA3 plasmid encoding the protein indicated in FIGS. 2A and 4 using FuGENE 6 transfection reagent. Transfected cells were collected at 40 hours post transfection, and RNA was extracted using trizol reagent (Invitrogen). An aliquot of the total RNA was analyzed by RNase protection using the uniformly labeled RNA probe shown in FIG. 2A, which was prepared as previously described (10). After annealing this labeled RNA probe to the cellular RNA sample, followed by digestion with RNAse A and phenol extraction, the protected RNA fragments were resolved by electrophoresis on a urea-polyacrylamide (5%) gel.

Generation of a recombinant influenza A/Udorn/72 virus encoding mutant 144 NS1A protein. Position 144 in the NS1A protein of influenza A/Udorn/72 virus was changed from L to A by PCR mutagenesis, and the resulting DNA was cloned into pHH21. This plasmid, plus the seven pHH21 plasmids encoding the other Udorn genomic RNAs, was cotransfected into 293T cells, along with the four plasmids encoding the PB1, PB2, PA and NP proteins. At 12 hours posttransfection, the media was changed to Opti-MEM supplemented with 3 µg/ml of NAT. After an additional 24-30 hours, the 293T cells were overlaid onto MDCK cells for virus amplification. Culture supernatants were collected when a positive HA assay titer was observed. Viruses were tittered by plaque assay on MDCK cells, and individual plaques were amplified in 10-day-old embryonic chicken eggs at 34° C. Amplified virus was tittered by plaque assay.

Measurement of IFN-β mRNA by real-time quantitative RT-PCR. RNA was isolated from infected cells using the trizol reagent at the indicated times after infection of MDCK cells. For each sample, 1 µg of total RNA, which corresponds to equal cell equivalents, was reverse transcribed using an oligo (dT) primer to generate the DNA complementary to all mRNAs. The amount of IFN-β mRNA was determined using the TaqMan Gene Expression Assay (Applied Biosystems) using 5' and 3' primers specific for canine IFN-β mRNA and a FAM dye-labeled TaqMan MGB (minor groove binder) internal probe. Real-time PCR analysis was carried out using the Perkin Elmer/Applied Biosystems 7900HT Sequence Detector.

Indirect immunofluoresence and confocal microscopy. Cells were fixed with 4% paraformaldehyde for 20 minutes, 0.5% Triton X-100 for another 10 minutes and then incubated with the indicated rabbit or mouse antibody at 37° C. for 1 hour. Following three washes in PBS, cells were incubated for 45 minutes with the secondary antibody, either fluorescein isothiocyanate-conjugated goat anti-rabbit antibody or rhodamine-conjugated goat anti-mouse antibody. The cells were examined by confocal microscopy as described previously (3).

Generation of a MDCK cell stably expressing the F2F3 protein fragment. The F2F3 protein fragment that was expressed in MDCK cells contained a N-terminal NLS (nuclear localization signal) from the SV40 T antigen (SEQ ID NO. 13: DPKKKKRKV) linked to the 61 amino acid F2F3 sequence from CPSF30, which in turn was linked at its C-terminus to 13 myc epitopes. The DNA sequence encoding this F2F3 fragment was produced using the pAJ1026plasmid, which contains 13 myc epitopes (13×SEQ ID NO. 14: EQKLISEEDL) (12). The NLS-F2F3 sequence containing a 5' EcoRI site was inserted into the N-terminus of the 13×myc sequence by PCR, which also generated a 3' EcoRI site. The fused sequence was excised using EcoRI and inserted into the EcoRI site of the pcDNA3 plasmid. In addition, as a control, we generated a F2F3 fragment containing a C-to-A mutation in the F2 (amino acid 76) and F3 (amino acid 105) zinc fingers. Another control was a pcDNA3 plasmid lacking an insert. MDCK cells were transfected by electroporation with 10 μg of ScaI-linearized plasmid. Forty-eight hours after transfection, DMEM containing 1.0 mg/ml neomycin sulfate was added, and the cells were incubated for approximately two weeks, at which time mock-transfected cells were all dead. Individual stable clones were picked and incubated with 25 μl trypsin-EDTA followed by plating onto 96-well tissue culture dishes. Each clone was grown and maintained in DMEM containing neomycin sulphate. For the cells tranfected with the pcDNA3 containing a F2F3insert, each cell clone was analyzed by immunoblots using myc antibody to identify the highest expressing cell clone.

Identification of the region of CPSF30 that binds to the influenza A virus NS1A protein. The influenza A virus NS1A protein binds CPSF30, a key component of the mammalian 3'-end processing machinery (10, 14). CPSF30 contains five C3H-zinc-finger repeats (1). To identify the region of CPSF30 that mediates its binding to the NS1A protein, we expressed GST fusions of N-terminal fragments of CPSF30 in bacteria and used these GST fusions in pulldown assays with labeled NS1A protein (FIG. 1A, lanes 3-5). These assays showed that the N-terminal fragment containing zinc fingers 1-3 (1-F3) is the shortest fragment that binds the NS1A protein. Deletion of the region N-terminal to zinc fingers 1-3, thereby generating the F1-F3 sequence, did not affect binding to the NS1A protein (lane 6), demonstrating that these three zinc fingers alone are sufficient for efficient binding to NS1A. In fact, the F1 zinc finger is not required, because F2F3, a 61-amino acid sequence, was sufficient for such binding (lane 7). The binding of F2F3 to NS1A requires the zinc finger structure, because a C-to-A mutation in either F2 (amino acid 76) or F3 (amino acid 105) greatly eliminated binding (data not shown).

The NS1A sequence centered at amino acid 186 is required for the binding of CPSF30 (10, 16). As shown in FIG. 1B, the NS1A sequence centered at amino acid 186 is also required for binding F2F3. Whereas GST-F2F3 efficiently bound labeled wild-type (wt) NS1A (lane 1), no detectable M186 NS1A protein bound to GST-F2F3 (lane 2).

Identification of the extent of the NS1A sequence that mediates inhibition of 3' end processing via F2F3 binding. Because the F2F3 fragment of CPSF30 is 61 amino acids long, it was reasonable to expect that its binding site on the NS1A protein includes amino acids in addition to those in the M186 region. To determine whether this is the case, an L-to-A substitutions was made at positions that are upstream (N-terminal) of position 186. The mutated NS1A proteins were assayed by expressing them in transient transfection studies to determine whether they retained the wild-type NS1A protein activity of inhibiting the 3' end processing of cellular pre-mRNAs. A plasmid expressing β-globin pre-mRNA provided the target pre-mRNA in these assays. The mutant NS1A protein containing a L-to-A substitution at position 141 retained wild-type activity (data not shown). In contrast, as shown in FIG. 2A, the mutant NS1A protein containing a L-to-A substitution at position 144 did not inhibit the 3' end processing of β-globin pre-mRNA, unlike the wt NS1A protein (compare lanes 2 and 3). In addition, this amino acid substitution eliminates most of the binding of the NS1A protein to the F2F3 fragment of CPSF30 (FIG. 2B). Only approximately 5-10% of wild-type binding to GST-F2F3 was observed with the M144 mutant protein (compare lanes 2 and 6). Therefore, the binding site of the F2F3 fragment that mediates the inhibition of 3' end processing encompasses the sequence of the NS1A protein from amino acid 144 to amino acids 184-188 (the 186 region).

Figure 3:
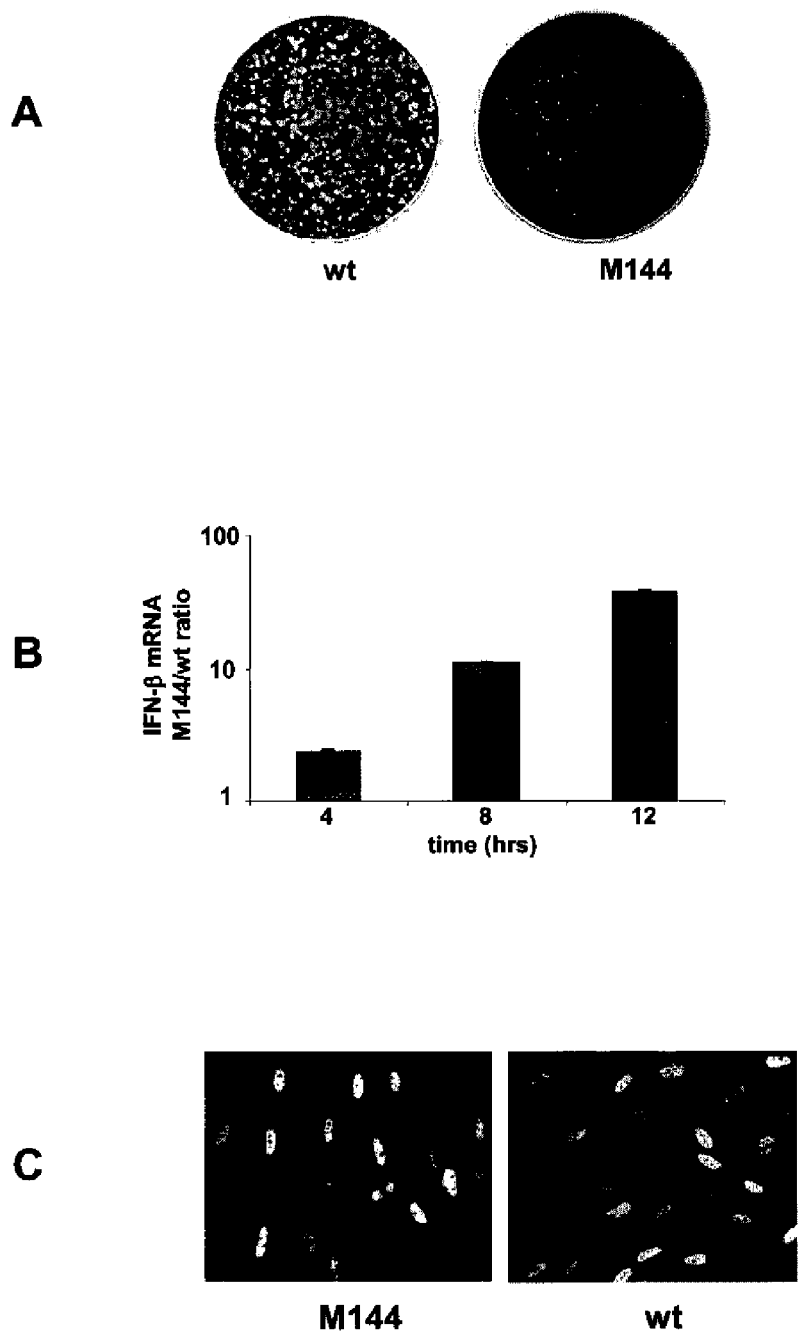
FIG. 3. Characterization of the M144 mutant virus. (A) Plaques formed by wt and M144 mutant viruses on MDCK cells. (B) The relative amounts of IFN-β mRNA produced during single cycle growth by M144 and wt virus. MDCK cells were infected with either M144 or wt virus at a moi of 5, and at the indicated times after infection the relative amounts of IFN-β mRNA produced was determined by quantitative RT-PCR. (C) Localization of the NS1A protein in cells infected by M144 and wt virus at 8 hours postinfection was determined by indirect immunofluorescence. The primary antibody was a rabbit polyclonal against the NS1A protein.

Next, a recombinant influenza A/Udorn virus was generated encoding a NS1A protein with a L-to-A substitution at position 144. The M144 mutant virus is attenuated: it forms pin-point plaques (FIG. 3A), and the rate of replication and virus yield at low multiplicity of infection (moi of 0.001 pfu/cell) was approximately 1000-fold lower than with wild-type virus (data not shown). This attenuation is attributable to the enhanced production of IFN-β mRNA in M144 virus-infected cells relative to wt virus-infected cells, as measured by quantitative RT-PCR (FIG. 3B). During single-cycle virus growth (moi of 5), the amount of IFN-β mRNA produced in M144 virus-infected cells at 8 and 12 hours post-infection was 12- and 40-times more, respectively, than that produced in wt virus-infected cells. A high moi was used under conditions that ensures that the amount of IFN-β mRNA produced per infected cell were measurable. In addition, under high moi conditions, approximately equal amounts of the NS1A protein were synthesized in wt virus- and M144 virus-infected cells (data not shown). The M144 mutant NS1A protein, like the wt NS1A protein, is localized in the nucleus of infected cells (FIG. 3C), demonstrating that the L-to-A substitution at position 144 does not affect the nuclear localization of the NS1A protein.

Inhibition of influenza A virus replication by F2F3. Because F2F3 binds strongly to the 144-186 region of the NS1A protein, it was also found that the F3F3 construct blocks the access of full-length endogenous CPSF30 to the NS1A protein and hence inhibits the replication of influenza A virus. A plasmid expressing a F2F3 molecule was constructed that includes an N-terminal nuclear localization signal (NLS) to ensure that the F2F3 is localized in the nucleus. In addition, 13 myc tags were added at the C-terminus of F2F3 to increase its size to 249 amino acids and to provide an epitope to analyze its production and localization. Transient transfection were carried out to determine whether high expression of this F2F3 protein construct inhibited endogenous CPSF30 function in the 3' end processing of cellular pre-mRNAs. As shown in FIG. 4, the F2F3 protein construct did not inhibit the 3' end processing of β-globin pre-mRNA, in contrast to the inhibition observed with the NS1A protein (compare lanes 2 and 3).

Figure 5:
FIG. 5. Characterization of the F2F3-expressing MDCK cells. (A) Localization of the F2F3 fragment was determined by indirect immunofluorescence using anti-myc antibody. (B) Determination of the relative amounts of the F2F3 protein fragment and the NS1A protein in influenza A virus-infected F2F3-expressing MDCK cells. An aliquot of the infected cells was analyzed by immunoblots using either anti-myc (left panel) or anti-NS1A antibody (right panel). To estimate the amount of the F2F3 protein fragment, increasing amounts of GST-NLS-13×myc was applied to the anti-myc immunoblot (left panel). The GST-NLS-13×myc was generated using the pAJ1026 plasmid, which contains 13 myc epitopes (12). Based on this immunoblot, as well as another immunoblot containing 10-30 ng of GST-NLS-13× myc, it was estimated that the aliquot from the virus-infected cells contains 10 ng of the F2F3 protein fragment. To estimate the amount of the NS1A protein, increasing amounts of GST-NS1A protein was applied to the anti-NS1A immunoblot (right panel). Based on this immunoblot, it was estimated that the aliquot from the virus-infected cells contains approximately 80 ng. Because the molecular weights of the F2F3 protein fragment and the NS1A protein are approximately the same, the molar ratio of the F2F3 fragment/NS1A protein was approximately 1/8.
Figure 5:
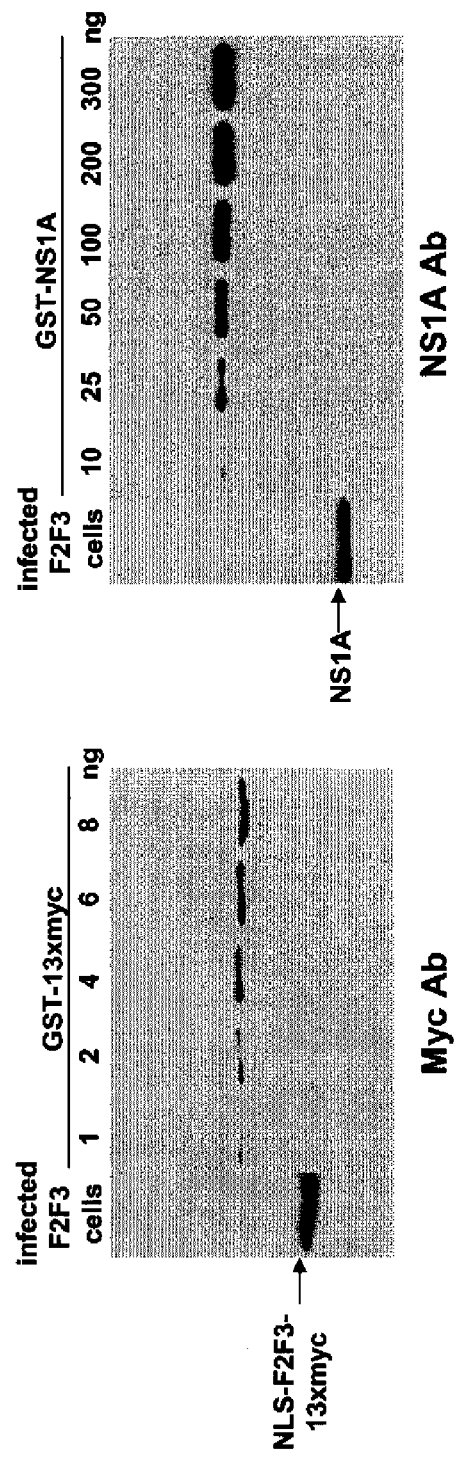

Based on the above results, it was expected that a cell line that constitutively expresses the F2F3 protein construct would effectively carry out the 3' end processing of cellular pre-mRNAs and hence would be viable. Consequently, such a cell was generated to determine whether the F2F3 protein construct inhibits influenza A virus replication. MDCK cells were transfected with a pcDNA3 plasmid expressing the F2F3 protein construct under the control of a CMV promoter. Forty (40) G418-resistant cell colonies were selected, and were screened by immunoblots using myc antiserum to identify the cells expressing the highest level of the F2F3 protein construct. The highest expressing MDCK cell line has been maintained in tissue culture for two years, and has not exhibited any discernible growth impediment. As shown in FIG. 5A, the expressed F2F3 protein construct is localized in the nucleus of these cells, demonstrating that the NLS at the N-terminus of the F2F3 construct is functional. In contrast, in cells expressing F2F3 constructs containing shorter epitope tags, e.g., the 3×FLAG epitope, the F2F3 construct was diffusely distributed throughout the cell and was not localized in the nucleus (data not shown), which led us to use the 13×myc epitope. Because the putative target of the F2F3 protein construct is the NS1A protein, we determined whether the F2F3 protein is expressed at a level comparable to that of the NS1A protein synthesized during influenza A virus infection. The F2F3-expressing cells were infected with influenza A virus at a moi of 5 to infect all the cells, and at 6 hours post-infection the amount of the F2F3 protein construct and the NS1A protein were estimated by immunoblots using either anti-myc or anti-NS1A antibody (FIG. 5B). Based on the protein standards, it was estimated that, on a molar basis, the F2F3 construct was present in approximately one-eighth the amount of the NS1A protein (see legend to FIG. 5B).

Although this is not an optimal F2F3/NS1A ratio, the inventors determined whether the replication of influenza A virus is inhibited in these cells. To generate control cell lines, MDCK cells were transfected with either an empty pcDNA3 plasmid or a pcDNA3 plasmid expressing a NLS-F2F3-13× myc construct containing a C-to-A mutation in the F2 and F3 zinc fingers, thereby eliminating the ability to bind to the NS1A protein. G418-resistant cells were then selected. However, the highest level of the mutant F2F3 construct that was expressed was only approximately 10% of the level of the wild-type F2F3 construct in the cell line analyzed in FIG. 5. The two control cell lines yielded identical results.

Figure 6:
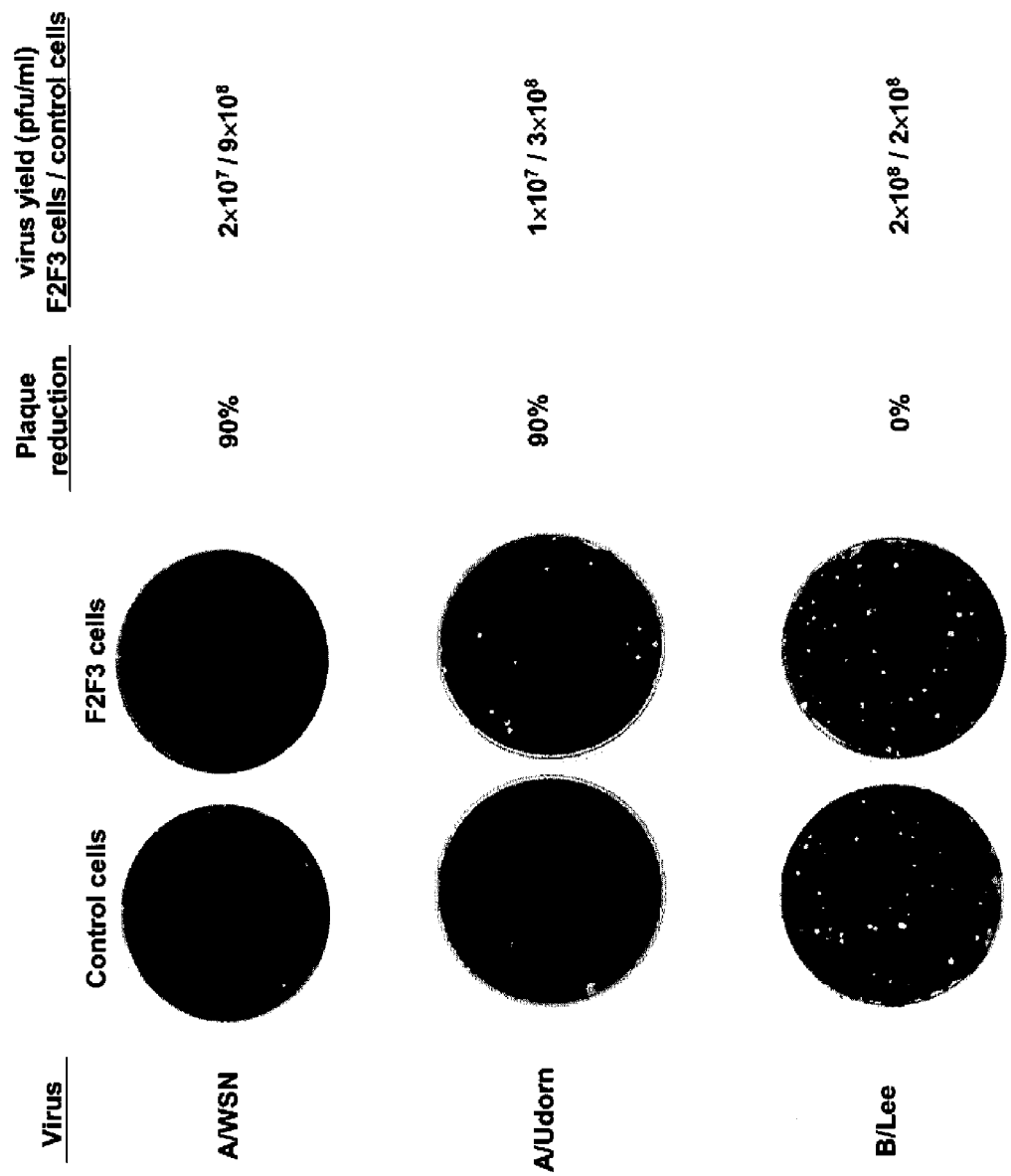
FIG. 6. Plaque reduction assays and virus yields after low moi infections in control and F2F3-expressing MDCK cells. The viruses used in these assays were influenza A/WSN/33, influenza A/Udorn/72, and influenza B/Lee/40.

As the first approach to monitor virus replication, a plaque reduction assay was employed. Monolayer cultures of the control and F2F3-expressing cells were infected with approximately 100 pfu of either influenza A/WSN/33 virus or influenza A/Udorn/72 virus per 60-mm culture dish and the viruses were allowed to form plaques under soft agar. The number of plaques on the F2F3-expressing cells was only approximately 10% of the number on the control cells (FIG. 6). To determine whether this 90% plaque reduction was specific for influenza A virus, the same assay was carried out with an influenza B virus (B/Lee/40), whose NS1B protein does not bind CPSF30 (16, 24). No reduction in plaque number of influenza B virus was observed in the F2F3-expressing cells compared to the control cells. The same selectivity was observed when virus yields were measured after low moi (0.001 pfu/cell) infections. The maximal yields of the two influenza A virus strains (36 hours at 37° C.) in the F2F3-expressing cells was 35-60-fold lower than in the control cells (FIG. 6). In contrast, the maximal virus yield of influenza B/Lee/40 virus (60 hours at 34° C.) was the same in both the control and the F2F3-expressing cells. It was found that the replication of influenza A virus, but not influenza B virus, is inhibited in the F2F3-expressing cells.

Figure 7A:
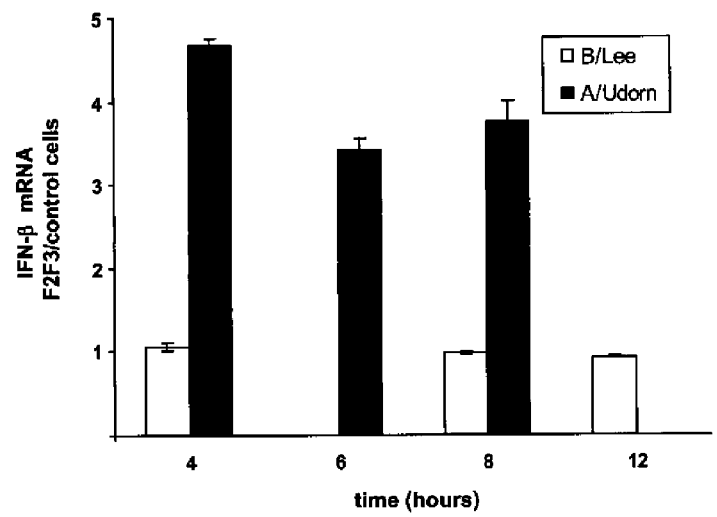
FIG. 7. Production of IFN-β mRNA and infectious virus during single-cycle growth in control and F2F3-expressing cells. (A) The relative amounts of IFN-β mRNA produced in F2F3-expressing and control cells after high moi infection (5 pfu/cell) with either influenza A/Udorn/72 or influenza B/Lee/40 virus. (B) Viral protein synthesis in F2F3-expressing and control cells after high moi infection with either influenza A/Udorn/72 virus (left panel) or influenza B/Lee/40 virus (right panel). At the indicated times after infection, cells were washed twice with methionine-free DMEM, 5 μl of a mixture of $^{35}$S-methionine and $^{35}$S-cysteine (Promix, Amersham) was added in a final volume of 1 ml of serum free DMEM, followed by incubation for 30 minutes. After incubation, cells were washed twice with PBS and lysed in 200 μL of Laemmli sample buffer. An aliquot was loaded onto SDS-polyacrylamide gels (12-15%) for analysis by autoradiography. (C) Replication of influenza A/Udorn/72 (left panel) and influenza B/Lee/40 (right panel) after high moi infection of F2F3-expressing and control cells.
Figure 7B:
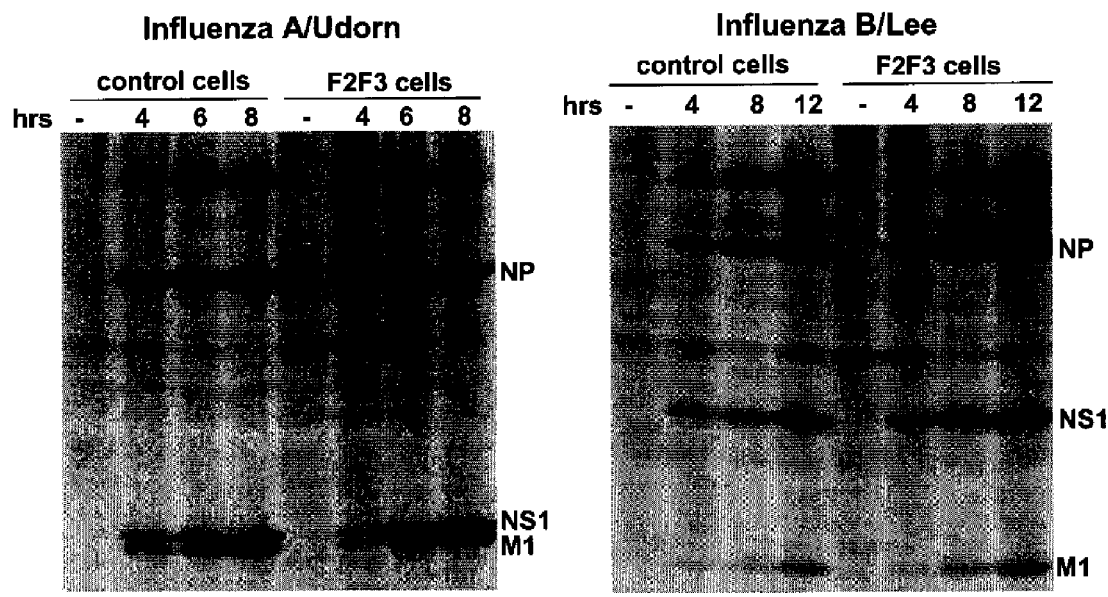
Figure 7C:
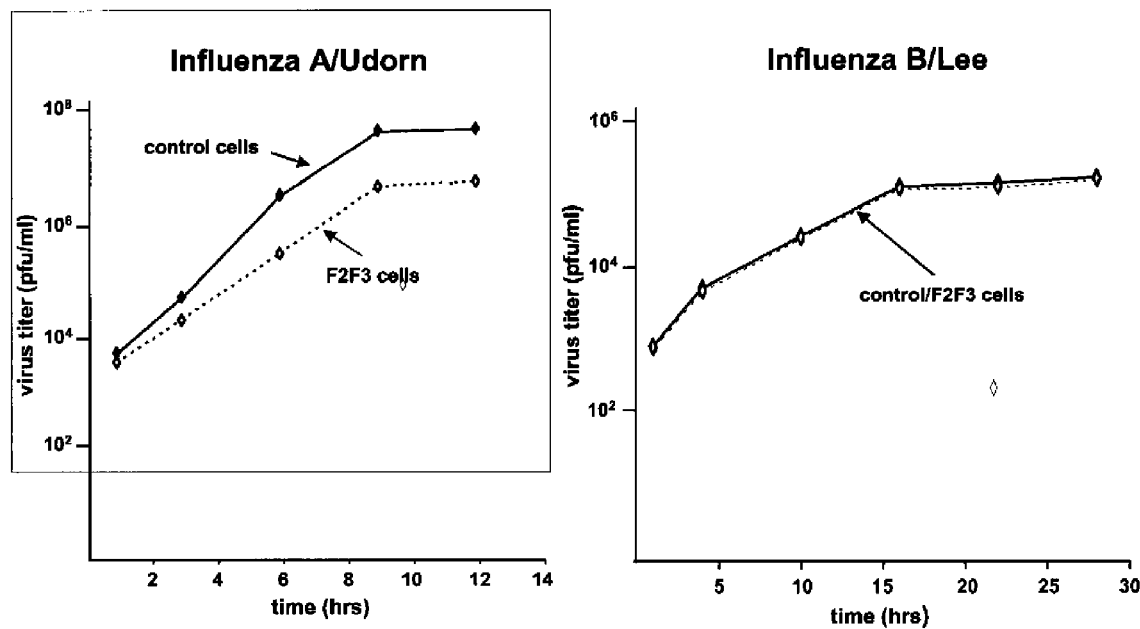

The selective inhibition of influenza A virus replication in the F2F3-expressing cells shows that the expressed F2F3 protein fragment selectively relieves the inhibition of the 3' end processing of IFN-β pre-mRNA mediated by the CPSF30 binding site on the NS1A protein. To determine whether this is the case, the amount of IFN-β mRNA produced per cell during single cycle growth after high moi infection with influenza A or influenza B virus was measured (FIG. 7A). The amount of IFN-β mRNA produced after influenza A virus infection was 3-5-fold higher in the F2F3-expressing cells than in the control cells. Equal amounts of the NS1A protein were synthesized after infection of the two cell lines (FIG. 7B), whereas virus replication was inhibited approximately 10-fold in the F2F3-expressing cells compared to the control cells (FIG. 7C). This level of inhibition is consistent with the 35-60-fold inhibition observed in the low moi multiple cycle infection. In contrast, the amount of IFN-β mRNA produced by influenza B virus was the same in the F2F3-expressing and control cells (FIG. 7A), and the replication of influenza B virus was not inhibited in the F2F3-expressing cells (FIGS. 7B and 7C). Therefore, the enhanced production of IFN-β mRNA is induced by influenza A virus in the F2F3-expressing cells and that this enhanced production is most likely responsible for the inhibition of influenza A virus replication during single cycle as well as multiple cycle infections.

The present invention also includes compositions and methods for the use of the influenza A virus NS1A protein that binds CPSF30 for targeting to inhibit influenza A virus replication. The binding of CPSF30 to the NS1A protein results in the inhibition of the 3' end processing of IFN-β pre-mRNA, as well as other cellular pre-mRNAs in influenza A virus-infected cells (16; present study). This inhibition is crucial, because influenza A virus, like several other RNA viruses, efficiently activates the RIG-I RNA helicase (13) to trigger the activation of IRF-3 and NF-κB and hence the synthesis of IFN-β pre-mRNA (6, 7, 13, 16). Because 3' end processing of the newly synthesized IFN-β pre-mRNA is inhibited by the NS1A protein, only a low amount of mature IFN-β mRNA is produced (16). Mutational inactivation of the NS1A site for binding CPSF30 results in increased IFN-β mRNA production and substantial attenuation of the virus (16; present study). For example, as shown here, the L-to-A mutation at position 144 results in a 40-fold increase in the amount of IFN-β mRNA produced during single cycle virus infection. Because mutations at both position 144 and in the 186 region of the NS1A protein result in this phenotype, the CPSF30 binding site on the NS1A protein likely includes the region between 144 and 186 (16; present study). A cell line expressing an F2F3 protein fragment was generated to investigate the effect of this mutation.

The highest expressing cell line produced an amount of the F2F3 fragment that was only one-eighth that of the NS1A protein produced during virus infection. Despite this relatively low level expression, influenza A virus replication was selectively inhibited in the F2F3-expressing cell line. The most dramatic evidence for this selective inhibition was obtained using plaque reduction assays. The number of influenza A virus plaques on the F2F3-expressing cells was only 10% of that on the control cells, whereas no plaque reduction was observed with influenza B virus.

In addition, virus yield after low moi infection with influenza A virus was reduced 35-60-fold in the F2F3-expressing cells compared to the control cells, whereas the virus yields of an influenza B virus was not reduced in the F2F3-expressing cells. Finally, during single cycle growth at high moi influenza A virus induced the synthesis of 3-5-fold more IFN-β mRNA in the F2F3-expressing cells compared to the control cells, and virus replication was inhibited by 10-fold in the F2F3-expressing cells. In contrast, influenza B virus did not induce more IFN-β mRNA in the F2F3-expressing cells, nor was its replication inhibited. These results provide strong support for the model shown in FIG. 8. Because the F2F3 fragment binds to the 144-186 region of the NS1A protein, it blocks the binding of full-length endogenous CPSF30. As a consequence, more IFN-β mRNA is produced, resulting in the inhibition of virus replication. The replication of influenza B virus is not inhibited because its NS1B protein lacks a binding site for CPSF30 and hence its F2F3 fragment (16, 24).

The ability of the F2F3 fragment to inhibit influenza A virus replication even though it is expressed at one-eighth the level of the NS1A protein indicates that targeting the F2F3 (and CPSF30) binding site on the NS1A protein is a promising approach for the development of antivirals directed against influenza A virus. In addition to the compositions and methods disclosed herein, small chemical compounds that bind strongly and specifically to the NS1A protein at its CPSF30 binding site will be effective inhibitors of influenza A virus replication. The concentration of such small chemical compounds that can be achieved in cells will greatly exceed the concentration of the F2F3 fragment achieved in the present study, resulting in a reduction of virus yield similar to that observed with mutational inactivation of the CPSF30 binding site on the NS1A protein.

Further, the lack of any apparent growth impediment of the F2F3-expressing cells during two years in tissue culture bodes well for the identification of small chemical compounds that bind with high specificity to the CPSF30 binding site on the NS1A protein without affecting the 3' end processing of host cell pre-mRNAs. It should be pointed out that the present study has already suggested an assay for the identification of such small molecule inhibitors of influenza A virus replication, specifically, a high-through-put assay to identify small chemical compounds that inhibit the binding of the F2F3 fragment to the NS1A protein. Small chemical compounds directed against the CPSF30 binding site of the NS1A protein would be expected to inhibit the replication of all strains of influenza A virus.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

1. Barabino, S. M., W. Hubner, A. Jenny, L. Minvielle-Sebastia, and W. Keller. 1997. The 30-kD subunit of mammalian cleavage and polyadenylation specificity factor and its yeast homolog are RNA-binding zinc finger proteins. Genes Dev 11:1703-16.

2. CDC (Center for Disease Control). 2005. Key facts about influenza and the influenza vaccine. http://www.cdc.gov/flu/keyfacts.htm.

3. Chen, Z., Y. Li, and R. M. Krug. 1999. Influenza A virus NS1 protein targets poly(A)-binding protein II of the cellular 3'-end processing machinery. EMBO J 18:2273-83.

4. Cox, N. J., and K. Subbarao. 1999. Influenza. Lancet 354:1277-82.

5. Ferguson, N. M., D. A. Cummings, S. Cauchemez, C. Fraser, S. Riley, A. Meeyai, S. Iamsirithaworn, and D. S. Burke. 2005. Strategies for containing an emerging influenza pandemic in Southeast Asia. Nature 437:209-14.

6. Geiss, G. K., M. Salvatore, T. M. Tumpey, V. S. Carter, X. Wang, C. F. Basler, J. K. Taubenberger, R. E. Bumgarner, P. Palese, M. G. Katze, and A. Garcia-Sastre. 2002. Cellular transcriptional profiling in influenza A virus-infected lung epithelial cells: the role of the nonstructural NS1 protein in the evasion of the host innate defense and its potential contribution to pandemic influenza. Proc Natl Acad Sci USA 99:10736-41.

7. Kim, M. J., A. G. Latham, and R. M. Krug. 2002. Human influenza viruses activate an interferon-independent transcription of cellular antiviral genes: outcome with influenza A virus is unique. Proc Natl Acad Sci USA 99:10096-101.

8. Kiso, M., K. Mitamura, Y. Sakai-Tagawa, K. Shiraishi, C. Kawakami, K. Kimura, F. G. Hayden, N. Sugaya, and Y. Kawaoka. 2004. Resistant influenza A viruses in children treated with oseltamivir: descriptive study. Lancet 364:759-65.

9. Le, Q. M., M. Kiso, K. Someya, Y. T. Sakai, T. H. Nguyen, K. H. Nguyen, N. D. Pham, H. H. Ngyen, S. Yamada, Y. Muramoto, T. Horimoto, A. Takada, H. Goto, T. Suzuki, Y. Suzuki, and Y. Kawaoka. 2005. Avian flu: isolation of drug-resistant H₅N₁ virus. Nature 437:1108.

10. Li, Y., Z. Y. Chen, W. Wang, C. C. Baker, and R. M. Krug. 2001. The 3'-end-processing factor CPSF is required for the splicing of single-intron pre-mRNAs in vivo. Rna 7:920-31.

11. Longini, I. M., Jr., A. Nizam, S. Xu, K. Ungchusak, W. Hanshaoworakul, D. A. Cummings, and M. E. Halloran. 2005. Containing pandemic influenza at the source. Science 309:1083-7.

12. Longtine, M. S., A. McKenzie, 3rd, D. J. Demarini, N. G. Shah, A. Wach, A. Brachat, P. Philippsen, and J. R. Pringle. 1998. Additional modules for versatile and economical PCR-based gene deletion and modification in *Saccharomyces cerevisiae*. Yeast 14:953-61.

13. Loo, Y.-M., Fredericksen, B., and Gale, M., Jr. 2005. Requirement of RIG-I in signaling the host response to virus infection. submitted for publication.

14. Nemeroff, M. E., S. M. Barabino, Y. Li, W. Keller, and R. M. Krug. 1998. Influenza virus NS1 protein interacts with the cellular 30 kDa subunit of CPSF and inhibits 3' end formation of cellular pre-mRNAs. Mol Cell 1:991-1000.

15. Nemeroff, M. E., X. Y. Qian, and R. M. Krug. 1995. The influenza virus NS1 protein forms multimers in vitro and in vivo. Virology 212:422-8.

16. Noah, D. L., K. Y. Twu, and R. M. Krug. 2003. Cellular antiviral responses against influenza A virus are countered at the posttranscriptional level by the viral NS1A protein via its binding to a cellular protein required for the 3' end processing of cellular pre-mRNAS. Virology 307: 386-95.

17. Puthavathana, P., P. Auewarakul, P. C. Charoenying, K. Sangsiriwut, P. Pooruk, K. Boonnak, R. Khanyok, P. Thawachsupa, R. Kijphati, and P. Sawanpanyalert. 2005. Molecular characterization of the complete genome of human influenza H5N1 virus isolates from Thailand. J Gen Virol 86:423-33.

18. Qiu, Y., and R. M. Krug. 1994. The influenza virus NS1 protein is a poly(A)-binding protein that inhibits nuclear export of mRNAs containing poly(A). J Virol 68:2425-32.

19. Reid, A. H., J. K. Taubenberger, and T. G. Fanning 2001. The 1918 Spanish influenza: integrating history and biology. Microbes Infect 3:81-87.

20. Shimizu, K., A. Iguchi, R. Gomyou, and Y. Ono. 1999. Influenza virus inhibits cleavage of the HSP70 pre-mRNAs at the polyadenylation site. Virology 254:213-9.

21. Suzuki, H., R. Saito, H. Masuda, H. Oshitani, M. Sato, and I. Sato. 2003. Emergence of amantadine-resistant influenza A viruses: epidemiological study. J Infect Chemother 9:195-200.

22. WHO (World Health Organization). 2005. Avian influenza. http://www.who.int/csr/disease/avian_influenza/en/

23. Wright, P. F., and R. G. Webster. 2001. Orthomyxoviruses, p. 1533-1579. In D. M. Knipe and P. M. Howley (ed.), Fields Virology, 4th Edition. Lippincott Williams & Wilkins, Philadelphia.

24. Yuan, W., and R. M. Krug. 2001. Influenza B virus NS1 protein inhibits conjugation of the interferon (IFN)-induced ubiquitin-like ISG15 protein. EMBO J 20:362-71.

What is claimed is:

1. A method of inhibiting Influenza A replication comprising:
   providing a pharmaceutical preparation comprising:
   (a) a pharmaceutical carrier and
   (b) a F2F3 zinc finger construct, wherein said construct is a fragment of a cleavage and polyadenylation specificity factor 30 kDa subunit (CPSF30) protein comprising a F2F3 zinc finger, or a polynucleotide construct encoding such a fragment, wherein the fragment inhibits Influenza A NS1A protein-mediated reduction of interferon-α and/or interferon-β and does not inhibit 3' end processing of cellular pre-mRNAs;
   administering an effective amount of the pharmaceutical preparation to one or more cells infected by influenza A virus; thus allowing the F2F3 zinc finger fragment to bind with and inhibit Influenza A NS1A protein activity and thus inhibiting Influenza A virus replication.

2. The method of claim 1, wherein the construct is a fragment of a cleavage and polyadenylation specificity factor 30 kDa subunit (CPSF30) protein comprising a F2F3 zinc finger.

3. The method of claim 1, wherein the construct is a polynucleotide encoding the fragment of a cleavage and polyadenylation specificity factor 30 kDa subunit (CPSF30) protein comprising a F2F3 zinc finger.

* * * * *

UNITED STATES PATENT AND TRADEMARK OFFICE
CERTIFICATE OF CORRECTION

PATENT NO. : 9,499,595 B2  
APPLICATION NO. : 12/554767  
DATED : November 22, 2016  
INVENTOR(S) : Robert M. Krug and Karen Y. Twu Page 1 of 1

It is certified that error appears in the above-identified patent and that said Letters Patent is hereby corrected as shown below:

On the Title Page

Item (73) Assignee, delete "BOARD OF REGENTS, THE UNIVERSITY OF TEXAS SYSTEMS" and insert --BOARD OF REGENTS, THE UNIVERSITY OF TEXAS SYSTEM-- therefor.

In the Specification

In Column 1, Lines 18-21, delete the entire contents of Lines 18-20 and insert --This invention was made with government support under Grant no. AI011772 awarded by the National Institutes of Health. The government has certain rights in the invention.-- therefor.

Signed and Sealed this  
First Day of May, 2018

Andrei Iancu  
*Director of the United States Patent and Trademark Office*